United States Patent [19]

Iimuro et al.

[11] Patent Number: 5,395,915

[45] Date of Patent: Mar. 7, 1995

[54] METHOD FOR SIMULTANEOUS PREPARATION OF BISPHENOL F AND NOVOLAK PHENOL RESINS

[75] Inventors: Shigeru Iimuro; Satoru Ito; Tomoko Takashima, all of Aichi; Takashi Kitamura, Kanagawa, all of Japan

[73] Assignee: Mitsui Toatsu Chemicals, Inc., Tokyo, Japan

[21] Appl. No.: 104,920

[22] Filed: Aug. 12, 1993

Related U.S. Application Data

[63] Continuation-in-part of Ser. No. 21,577, Feb. 24, 1993.

[51] Int. Cl.6 .................. C08G 14/02; C08G 8/04
[52] U.S. Cl. .................... 528/137; 528/129; 528/144; 568/727; 568/724
[58] Field of Search ............ 528/129, 137, 144; 568/727, 224, 727

[56] References Cited

U.S. PATENT DOCUMENTS

4,937,392  5/1990  Imanari et al. .............. 568/727

FOREIGN PATENT DOCUMENTS

62-119220  5/1987  Japan .
2-70721    3/1990  Japan .
3-24115    2/1991  Japan .
4-68020    3/1992  Japan .

OTHER PUBLICATIONS

Moss, W. H. & Moss, Elsie, Brit. Polym. J 1(1) 29–33, 1969. "Isolation of Dinuclear dihydroxydiphonylmethanes & Trinuclear Novolaks (triphenylols) from PF condensations".

*Primary Examiner*—John Kight, III
*Assistant Examiner*—Richard Jones
*Attorney, Agent, or Firm*—Burns, Doane, Swecker & Mathis

[57] ABSTRACT

Herein disclosed is a method for simultaneously preparing a highly pure bisphenol F and/or a bisphenol F for general use and a novolak phenol resin and/or a high molecular weight novolak phenol resin comprising the steps of:

(1) a preparation step comprising reacting phenol with formaldehyde in the presence of an acid catalyst and removing the acid catalyst, water and the unreacted phenol from the resulting reaction product to give a crude bisphenol F;

(2) a distillation step comprising distilling a part of the crude bisphenol F to give a highly pure bisphenol F, as a distillate, having a binuclear moiety-content of not less than 95% by weight and a novolak phenol resin, as a still-bottom product, having a binuclear moiety-content of not more than 15% by area;

(3) a step for mixing the highly pure bisphenol F with the remaining crude bisphenol F to give a bisphenol F for general use; and (4) a step for polymerizing the novolak phenol resin with formaldehyde in the presence of an acid catalyst to give a high molecular weight novolak phenol resin.

24 Claims, 5 Drawing Sheets

METHOD FOR SIMULTANEOUS PREPARATION OF BISPHENOL F AND NOVOLAK PHENOL RESINS

CROSS-REFERENCES TO RELATED APPLICATION

This is a continuation-in-part application of U.S. patent application Ser. No. 08/021,577, filed on Feb. 24, 1993.

BACKGROUND OF THE INVENTION

(a) Field of the Invention

Recently, there has been desired the development of highly pure bisphenol F having a high binuclear moiety-content and bisphenol F for general use, such as starting materials for epoxy and polycarbonate resins. On the other hand, various kinds of novolak phenol resins have been used as resist materials, binders for producing molds, hardeners for epoxy resins or base resins for epoxy resins and recently, they have widely been used, in particular, in the field of electric and electronic materials.

The present invention relates to a method for simultaneously preparing bisphenol F and a novolak phenol resin and more specifically to a method for simultaneously preparing highly pure bisphenol F having a high binuclear moiety-content and/or bisphenol F for general use as well as a novolak phenol resin having a low binuclear moiety-content, but having high contents of trinuclear and tetranuclear moieties, in particular, trinuclear moieties and a high molecular weight novolak phenol resin having a low binuclear moiety-content and a high trinuclear moiety-content.

(b) Description of the Prior Art

Both bisphenol F and novolak phenol resins are prepared from a stoichiometrically excess phenol to formaldehyde in the presence of an acid catalyst. These are different, from one another, in the reaction molar ratio of phenol to formaldehyde (hereinafter referred to as "P/F").

In general, bisphenol F is prepared at a P/F ranging from 20 to 50 and the reaction product comprises three kinds of binuclear moieties, i.e., 4,4'-dihydroxydiphenylmethane (hereinafter referred to as "4,4'-moiety"), 2,4'-dihydroxydiphenylmethane (hereinafter referred to as "2,4'-moiety") and 2,2'-dihydroxydiphenylmethane (hereinafter referred to as "2,2'-moiety") as well as 7 to 12% by weight of 3-nuclear (trinuclear) to 5-nuclear (pentanuclear) moieties (hereinafter also referred to as "polynuclear moieies") formed through polycondensation of phenol and formaldehyde.

It has been known that the polynuclear moieties greatly affect the physical properties of an epoxy resin obtained through epoxidation of bisphenol F. This means that the resulting epoxy resin is liable to cause crystallization as the content of the polynuclear moieties decreases, while if the content thereof increases, the viscosity of the epoxy resin becomes high and this impairs the workability thereof.

First of all, bisphenol F for general use will hereinafter be explained in detail.

Bisphenol F for general use is a bisphenol F which comprises binuclear moieties in an amount ranging from about 88 to 93% by weight and preferably about 90 to 93% by weight and has effectively been used as a starting material for epoxy resins having a low viscosity.

Japanese Unexamined Patent Publication (hereinafter referred to as "J. P. KOKAI") No. Sho 55-124730 discloses a method for preparing bisphenol F for general use. According to this method, bisphenol F useful as a starting material for epoxy resins can be obtained by limiting the reaction molar ratio (P/F) of phenol to formaldehyde to the range of from 25 to 50.

In addition, J. P. KOKAI No. Sho 63-238032 discloses that the use of activated china clay as a catalyst permits the production of bisphenol F suitable as a starting material for epoxy resins even if the foregoing reaction molar ratio is reduced to a level of the order of 20. In this method, however, the rate of bisphenol F produced with respect to the reaction mass is low in the order of about 0.1 although the reaction molar ratio (P/F) is about 20. This results in the reduction of production efficiency and requires a great deal of energy for the separation of the excess phenol.

Now highly pure bisphenol F will be explained below.

Highly pure bisphenol F is a bisphenol F whose binuclear moiety-content is greater than that of the bisphenol F for general use and is effectively used as a starting material for preparing epoxy resins for paint and varnish.

J. P. KOKAI No. Hei 2-166114 discloses that paint and varnish which comprise an epoxy resin prepared from a bisphenol F having a binuclear moiety-content of not less than 95% by weight, preferably not less than 98% by weight are excellent in, for instance, corrosion resistance and the resistance to chemicals of the resulting films is high compared with those achieved by paint and varnish which comprise an epoxy resin prepared from a bisphenol F having a binuclear moiety-content of 92% by weight.

However, it has been impossible for any conventional technique to prepare highly pure bisphenol F having a binuclear moiety-content of not less than 98% by weight through the reaction of phenol and formaldehyde even if the reaction molar ratio, P/F, is increased up to 100 or higher. In other words, the formation of such highly pure bisphenol F is industrially impracticable.

For instance, when a continuous equilibrium flash distillation is carried out after removing the unreacted phenol from the reaction product obtained through the reaction of phenol and formaldehyde, it is necessary, on the basis of the gas-liquid equilibrium, to control the binuclear moiety-content in a still-bottom product to not less than 30% by weight in order to obtain a distillate having a binuclear moiety-content of not less than 98% by weight. In such a method, however, a large amount of useful binuclear moieties remain in the still-bottom product and this makes the method less economical.

Japanese Examined Patent Publication (hereinafter referred to as "J. P. KOKOKU") No. Sho 39-8399 discloses a method for preparing highly pure bisphenol F. The object of this invention is to obtain a reaction product as a mixture of isomers thereof whose content of 4,4'-moiety falls within the range of from 40 to 80% by weight. This method comprises the steps of subjecting a reaction product to batch-wise simple distillation over two times to give a mixture mainly comprising binuclear moieties and then recrystallizing the mixture from toluene to give highly pure bisphenol F. However, this invention does not disclose the composition of the still-bottom product remaining in the still after the batch-wise simple distillation performed twice, the contents of useful binuclear moieties and polynuclear moieties included in the filtrate obtained after the recrystallization and methods for recovering the same. Moreover, the recovery of the useful components from the filtrate obtained after the recrystallization requires evaporation of a large amount of solvents used and hence a great deal of energy.

Novolak phenol resins will now be explained below.

A novolak phenol resin is a resin generally prepared through a reaction of phenol and formaldehyde at a P/F of 1 to 2 and having an average number of nuclear moieties of 4 to 5 and a binuclear moiety-content of 10 to 30% by weight.

It has been known that the distribution of these moieties in a novolak phenol resin is determined by the molar ratio, P/F, of phenol to formaldehyde. For instance, the reaction of phenol and formaldehyde performed at a P/F of 2 can provide a novolak phenol resin which comprises about 25% by area of binuclear moieties, about 20% by area of trinuclear moieties and about 15% by area of tetranuclear moieties. The higher the P/F ratio, the greater the binuclear moiety-content and the lower the softening point of the resulting resin.

The term "% by area" used herein for expressing the content of each moiety present in novolak phenol resins and high molecular weight novolak phenol resins is determined by subjecting these resins to gel permeation chromatography (using two columns, G4000HXL+G2500HXL+G2000HXL, available from Tosoh Corporation; eluent: tetrahydrofuran).

When the novolak phenol resin is used as a starting material or a hardener for epoxy resins, inconveniences such as the formation of flashes on molded articles and/or reduction of strength due to a decrease in the degree of crosslinking occur. For this reason, there has been desired for the development of a novolak phenol resin having a low binuclear moiety-content.

Moreover, it has also been desired for the development of a technique for reducing the contents of unreacted starting materials which do not contribute to crosslinking reactions and those of binuclear or lower moieties present in novolak phenol resins for improving the strength of the cured product when it is used as a hardener or a base resin for epoxy resin.

On the other hand, one of the important properties required for phenol resins is low viscosity. If the viscosity of phenol resins can be lowered while maintaining other characteristic properties such as heat resistance and strength, the workability, reactivity, flow properties and impregnating properties thereof would be greatly improved. Moreover, this permits incorporation of fillers such as inorganic fillers into these resins depending on applications.

In case where the resins are used as binders for producing molds, the resins must have low contents of binuclear or lower moieties, i.e., binuclear moieties and unreacted starting materials included in the resins in order to reduce the amount of smuts possibly generated during molding operations.

Further it has likewise been required for phenolic hardeners for use in epoxy resins which are used for electric and electronic applications, whose demand has rapidly been increased recently, to have low viscosities and low contents of binuclear moieties.

In general, phenol and formaldehyde are reacted at a low P/F ratio ranging from 2 to 3 to give a low molecular weight resin, i.e., a low viscosity resin. However, such a low viscosity resin has high contents of binuclear or lower moieties which do not contribute to crosslinking reactions. Therefore, if such a low molecular weight resin is used as a hardener, the hardness of the cured product is impaired.

For instance, when the reaction is carried out at a P/F ratio of 5/2 to reduce the viscosity, the resulting resin has a low molecular weight and a low melt viscosity. However, the reaction product has high contents of binuclear or lower moieties which do not contribute to crosslinking reactions and this leads to formation of products, during hardening reaction, which have insufficient strength. Accordingly, if the binuclear moieties are further removed, the resulting resin comprises about 35% by area of trinuclear moieties and about 23% by area of tetranuclear moieties in addition to binuclear moieties whose amount has been reduced. This resin can provide hardened products having sufficient strength, but cannot achieve a sufficiently low viscosity since the binuclear moieties are removed to a substantially low level.

Thus, when the reaction is performed at a P/F ratio of, for instance, 5/4 so as to reduce the amount of binuclear moieties formed, the resulting novolak phenol resin comprises 9% by area of binuclear moieties, 8% by area of trinuclear moieties and 6% by area of tetranuclear moieties. In this case, the contents of binuclear moieties are reduced, while those of high molecular weight reaction products formed during the reaction increase. This leads to an increase of viscosity and accordingly becomes a cause of various problems such as reduction of workability, reactivity, flow properties and impregnating properties.

In order to reduce the content of binuclear moieties present in a novolak phenol resin according to the conventional methods, the ratio, P/F, is necessarily reduced, but this leads to increases of the softening point and viscosity of the resulting novolak resin and this leads to deterioration of the flow properties of the resin during molding.

Under such circumstances, there has recently been tried to further reduce the content of binuclear moieties by dehydrating an initial condensate formed through a reaction, removing phenol as a starting material and then removing binuclear moieties through an operation such as extraction, steam distillation or distillation under reduced pressure. In this case, the removal of the binuclear moieties results in the formation of a hardened product having a strength higher than that achieved by the resin having a high content of binuclear moieties, but the viscosity of the product is correspondingly increased.

There have been known methods for preparing novolak phenol resins having low content of binuclear moieties. For instance, J. P. KOHYO No. Sho 62-501780 discloses a method comprising extracting binuclear moieties with hot water after the reaction of phenol and formaldehyde and J. P. KOKAI No. Hei 2-60915 discloses a method which comprises adding a solvent slightly soluble in water and then adding a water-soluble alcohol and water to remove components having small numbers of nuclei.

However, these method do not disclose any effective use of the binuclear moieties thus removed at all. Consequently, about 20% by weight of binuclear moieties, on the basis of the novolak phenol resin, are discarded. Moreover, the recovery of the useful binuclear moieties according to these methods requires evaporation of a large quantity of water and solvents used and this in turn leads to the consumption of a great deal of energy.

As binders for producing molds, there have been known, for instance, J. P. KOKAI No. Sho 60-133017 which discloses those having low contents of binuclear moieties and those of hexanuclear or higher moieties. However, the viscosity of the resin is still too high.

J. P. KOKAI Nos. Sho 62-267314, Sho 62-275121 and Sho 62-277419 disclose resins whose contents of binuclear moieties are lowered, but the viscosity thereof is still too high.

J. P. KOKAI No. Hei 2-70721 discloses an epoxy resin composition comprising, as a hardener, a novolak phenol resin whose binuclear moiety-content is not less than 1.0% by weight and not more than 5.0% by weight, whose softening point is not less than 80° C. and not more than 120° C. and whose number-average molecular weight is not less than 300 and not more than 900. This patent discloses that the resin is in general prepared by reacting formaldehyde with phenol in a reaction molar ratio ranging from 1:1 to 1:2.5. More specifically, formaldehyde is reacted with phenol in an amount of 1 to 2.5 times the molar amount of formaldehyde, the unreacted phenol is removed from the reaction system and then the binuclear moiety-content thereof is reduced to thus give a desired resin having a high degree of crosslinking. However, the viscosity of the resulting resin is too high to increase the amount of a filler to be added for reducing the linear expansion coefficient of the resin.

J. P. KOKAI No. Hei 3-24115 discloses an epoxy resin composition comprising, as a hardener for an epoxy resin, a novolak phenol resin whose binuclear moiety-content is not less than 20% by weight and whose content of the sum of binuclear and trinuclear moieties is not less than 35% by weight. The novolak phenol resin is a low molecular weight hardener and correspondingly has a low viscosity. Thus, the hardener permits an increase in the amount of a filler to be added such as an inorganic filler and in turn reduction of the linear expansion coefficient of the resin. However, the resin having a high content of binuclear moieties does not permit the improvement of the heat resistance of the resulting cured product and the high contant of volatile matter thereof does not permit any reduction of the rate of crack-formation.

J. P. KOKAI No. Hei 4-68020 discloses an epoxy resin composition comprising a liquid epoxy resin as an epoxy resin component and, as a hardener, a novolak phenol resin whose content of trinuclear moieties is not less than 80% by weight and whose softening point is not higher than 85° C. However, this patent does not discloses any method for preparing the novolak phenol resin and the components of the resin other than the trinuclear moieties.

J. P. KOKAI No. Sho 62-119220 discloses a method for preparing a polyhydroxy compound having a content of the sum of binuclear and lower moieties of not more than 5% by weight and a content of trinuclear moieties of not less than 30% by weight. This patent discloses that the polyhydroxy compound can be prepared by reacting a dimethylol derivative of a substituted phenol as a starting material with phenol in the presence of a basic catalyst and then neutralizing the reaction product with an acid.

Therefore, the use of the conventional reaction molar ratio has never permitted the production of any novolak phenol resin having a low melt viscosity while maintaining the reliability of other desired characteristic properties such as mechanical strength and heat resistance, even if the contents of binuclear moieties is reduced.

SUMMARY OF THE INVENTION

The object of the present invention is generally to solve the aforementioned problems associated with the conventional techniques and more specifically to provide a method for simultaneously preparing highly pure bisphenol F whose content of binuclear moieties is not less than 95% by weight and/or bisphenol F for general use and a novolak phenol resin and/or a high molecular weight novolak phenol resin having a binuclear moiety-content of not more than 15% by area.

The inventors of this invention have conducted intensive studies to accomplish the foregoing object, have found out that the object can effectively be achieved by making the most use of a still-bottom product obtained after the distillation of a crude bisphenol F product and thus have completed the present invention.

According to a first embodiment of the present invention, there is provided a method for simultaneously preparing highly pure bisphenol F and a novolak phenol resin which comprises the steps of:

(1) a preparation step comprising reacting phenol with formaldehyde in the presence of an acid catalyst and removing the acid catalyst, water and the unreacted phenol from the resulting reaction product to give a crude bisphenol F; and (2) a distillation step comprising distilling the crude bisphenol F to give highly pure bisphenol F, as a distillate, having a binuclear moiety-content of not less than 95% by weight, preferably not less than 98% by weight and a novolak phenol resin, as a still-bottom product, having a binuclear moiety-content of not more than 15% by area, preferably not more than 10% by area.

According to a second embodiment of the present invention, there is provided a method for simultaneously preparing bisphenol F for general use and a novolak phenol resin which comprises the steps of:

(1) a preparation step comprising reacting phenol with formaldehyde in the presence of an acid catalyst and removing the acid catalyst, water and the unreacted phenol from the resulting reaction product to give a crude bisphenol F;

(2) a distillation step comprising distilling a part of the crude bisphenol F to give highly pure bisphenol F, as a distillate, having a binuclear moiety-content of not less than 95% by weight, preferably not less than 98% by weight and a novolak phenol resin, as a still-bottom product, having a binuclear moiety-content of not more than 15% by area, preferably not more than 10% by area; and (3) a step of admixing the highly pure bisphenol F with the remaining crude bisphenol F to give bisphenol F for general use.

According to a third embodiment of the present invention, there is provided a method for simultaneously preparing highly pure bisphenol F, bisphenol F for general use and a novolak phenol resin which comprises the steps of:

(1) a preparation step comprising reacting phenol with formaldehyde in the presence of an acid catalyst and removing the acid catalyst, water and the unreacted phenol from the resulting reaction product to give a crude bisphenol F;

(2) a distillation step comprising distilling a part of the crude bisphenol F to give highly pure bisphenol F, as a distillate, having a binuclear moiety-content of not less than 95% by weight, preferably not less than 98% by weight and a novolak phenol resin, as a still-bottom product, having a binuclear moiety-content of not more than 15% by area, preferably not more than 10% by area; and (3) a step of mixing a part of the highly pure bisphenol F with the remaining crude bisphenol F to give bisphenol F for general use.

According to a fourth embodiment of the present invention, there is provided a method for simultaneously preparing highly pure bisphenol F and/or bisphenol F for general use and a high molecular weight novolak phenol resin which comprises a polymerization step for reacting the novolak phenol resin obtained according to the foregoing first, second or third embodiment with formaldehyde in the presence of an acid catalyst to give a high molecular weight novolak phenol resin. In this case, it is also possible to polymerize only a part of the novolak phenol resin to obtain both novolak phenol resin and high molecular weight novolak phenol resin.

The distillation step in the simultaneous production method according to the present invention is preferably performed by providing a distillation apparatus equipped with a still, a partial condenser and a complete condenser; continuously supplying the crude bisphenol F to the still maintained at a temperature ranging from 220° to 250° C. and a pressure ranging from 1 to 5 mm Hg; and continuously distilling the crude bisphenol F while partially condensing a part of the evaporated gases in the partial condenser, returning the condensate to the still and continuously withdrawing the still-bottom product, or providing a distillation apparatus equipped with a plurality of stills arranged in series, at least one partial condenser and at least one complete condenser, continuously supplying the crude bisphenol F to a first still among the plurality of stills maintained at a temperature ranging from 200° to 250° C. and a pressure ranging from 1 to 5 mm Hg; and continuously distilling the crude bisphenol F while supplying the still-bottom product of each still to the subsequent still, partially condensing a part of evaporated gases discharged from a final still maintained at a temperature ranging from 220° to 250° C. and a pressure ranging from 1 to 5 mm Hg to return the condensate to the final still and continuously withdrawing the still-bottom product from the final still. In this case, it is preferred to use, as the partial condenser, a multi-tubular cylindrical heat exchanger or a coil heat exchanger and to limit the partial-condensation ratio (weight ratio) to the range of from 0.05 to 0.5.

BRIEF DESCRIPTION OF THE DRAWINGS

In FIGS. 3 to 10, characters ②, ③, ④, ⑤ and ⑥ each represent binuclear, trinuclear, tetranuclear, pentanuclear or hexanuclear moieties.

DESCRIPTION OF THE PREFERRED EMBODIMENTS

Figure 1:
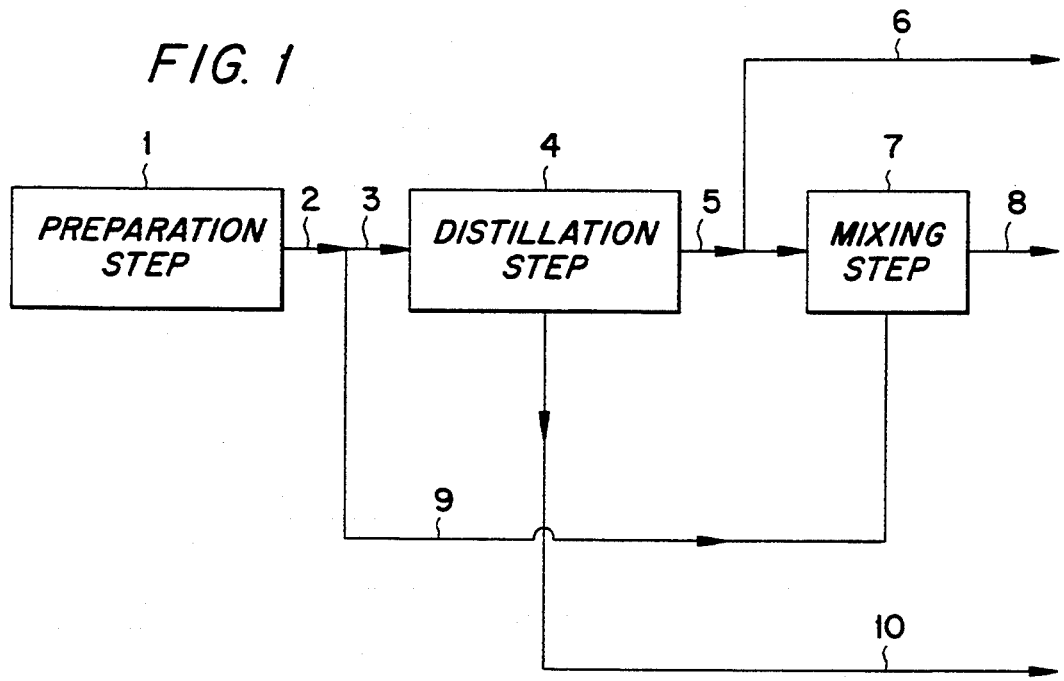
FIG. 1 is a system diagram showing a typical embodiment according to the present invention.

The method according to the present invention will hereinafter be explained in more detail.

The term "crude bisphenol F" herein used means a product obtained by reacting phenol and formaldehyde in the presence of an acid catalyst and then removing the acid catalyst, the water and unreacted starting materials from the resulting reaction mixture.

The term "highly pure bisphenol F" herein used means bisphenol F comprising binuclear moieties in an amount of not less than 95% by weight and preferably not less than 98% by weight, while the term "bisphenol F for general use" herein means bisphenol F comprising binuclear moieties in an amount ranging from 88 to 93% by weight.

Further, the term "novolak phenol resin" herein used means novolak phenol resins whose content of binuclear moieties is not more than 15% by area and the term "high molecular weight novolak phenol resin" means a still-bottom product obtained through the distillation step of the method of this invention which is a product obtained by reacting a novolak phenol resin with formaldehyde in the presence of an acid catalyst and preferably a high molecular weight novolak phenol resin having a weight-average molecular weight of higher than 340 and a binuclear moiety-content of not more than 10% by area.

Particularly preferred novolak phenol resins according to the present invention are those having a nuclear number-distribution such that the binuclear moiety-content thereof is low and the contents of trinuclear and tetranuclear moieties, in particular, the trinuclear moiety-content are high. The novolak phenol resin of the present invention having a low melt viscosity which has never been achieved and which can provide a hardened product having a high degree of crosslinking comprises the resin having such a nuclear number-distribution peculiar thereto.

The binuclear moiety-content of the novolak phenol resin is preferably low and in general not more than 15% by area and preferably not more than 10% by area. This is because the binuclear moieties do not make any contribution to the crosslinking reaction thereof. However, an increase of the binuclear moiety-content permits a decrease of the viscosity of the resin and, therefore, the binuclear moieties may be comprised in the resin in such an amount that the presence thereof does not adversely affect the required degree of crosslinking.

The trinuclear moiety-content of the novolak phenol resin is preferably not less than 50% by area on the basis of the total quantity of the resin other than the binuclear moiety-content. The novolak phenol resin having a desired low melt viscosity can thus be obtained by the control of the trinuclear moiety-content to not less than 50% by area.

The content of the sum of trinuclear and tetranuclear moieties is preferably not less than 80% by area on the basis of the resin other than the binuclear moiety. The contents of trinuclear and higher nuclear moieties are preferably high since the binuclear and lower nuclear moieties, i.e., unreacted phenol and the binuclear moieties do not take part in the crosslinking reaction of the resin. On the other hand, the greater the content of low molecular weight components, the lower the melt viscosity of the resulting resin. For this reason, the content of the sum of the trinuclear and tetranuclear moieties present in the novolak phenol resin is preferably adjusted to not less than 80% by area and thus a desired resin having a low melt viscosity can be obtained.

The binuclear moiety-content in the high molecular weight novolak phenol resin is determined by that in the novolak phenol resin and the amount of formaldehyde used. As has been described above, the binuclear and lower moieties, i.e., unreacted phenol and the binuclear moieties do not take part in the crosslinking reaction of the resin and, therefore, the content thereof in the high molecular weight novolak phenol resin should be limited to a low level in order to improve the strength of the resulting hardened product. On the other hand, the higher the binuclear moiety-content, the lower the viscosity of the resin. For this reason, the resin may contain the binuclear moieties as long as they do not adversely affect the strength of the hardened product. The binuclear moiety-content of the resin is preferably not more than 10% by area.

The trinuclear moiety-content y on the basis of the high molecular weight novolak phenol resin from which the binuclear moiety-content is subtracted preferably has the following relation with respect to the number-average molecular weight x of the resin:

$$y \geq 7900/(x-210) \text{ (wherein } x=300\sim800)$$

and the resin preferably has a high trinuclear moiety-content. In this case, there can be obtained a high molecular weight novolak phenol resin having a low melt viscosity which cannot be achieved by the novolak phenol resin having the same glass transition temperature (hereinafter referred to as "Tg") as determined after hardening the resin.

Figure 2:
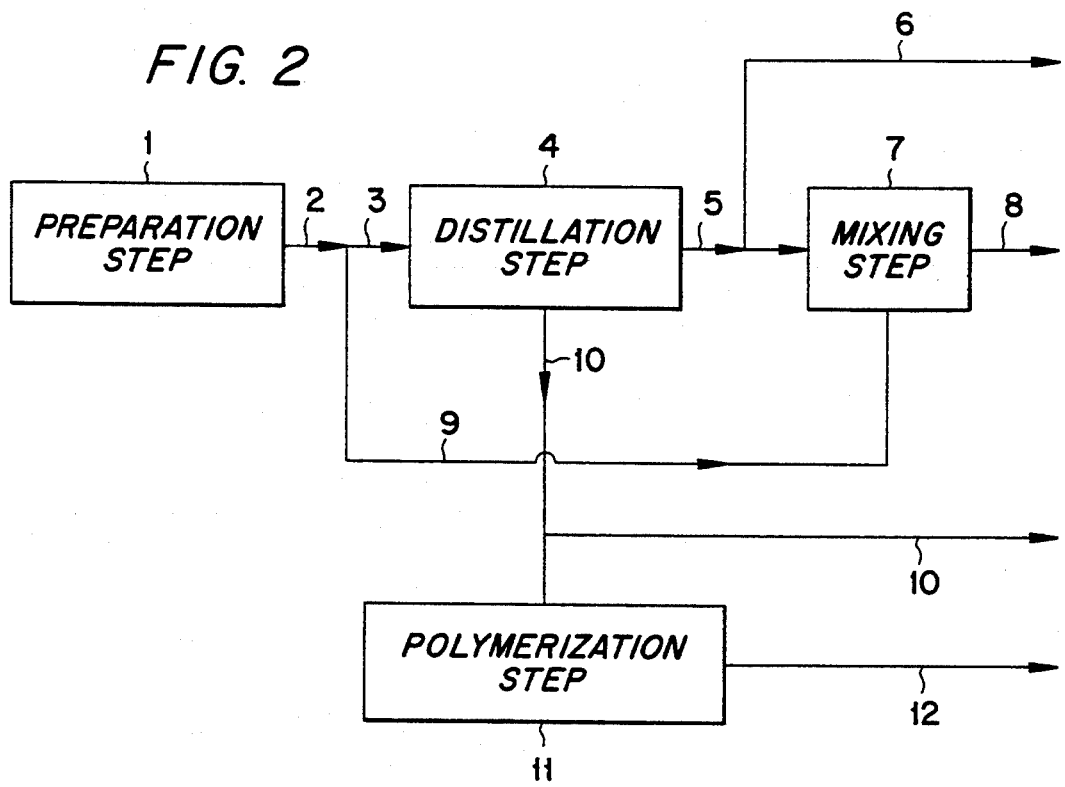
FIG. 2 is a system diagram showing another typical embodiment according to the present invention.

The present invention will hereinafter be explained with reference to the attached FIG. 1 or 2.

First of all, the method for simultaneously preparing highly pure bisphenol F 6 and novolak phenol resin 10 having a low binuclear moiety-content will be explained according to the first embodiment of the present invention.

Stoichiometrically excess phenol and formaldehyde are introduced into a preparation step 1 (from a reaction step to a phenol-removal step). More specifically, to a reactor equipped with, for instance, a stirring machine, a temperature control device, a reflux condenser, a complete condenser and a vacuum device, there are charged phenol, formaldehyde and an acid catalyst and these ingredients are reacted at a determined temperature for a desired period with stirring. Then the acid catalyst, the water formed during the reaction and the unreacted phenol are removed from the reaction product to give crude bisphenol F 2.

The phenol component used in the invention may be, for instance, cresol and o-, m- or p-substituted alkylphenols in addition to phenol.

Examples of the formaldehyde components usable herein are formalin, paraformaldehyde, hexamethylenetetramine, trioxane and cyclic formal.

The reaction molar ratio, P/F, is in general not less than 6, preferably 6 to 30 and more preferably 6 to 20. The higher the reaction molar ratio: P/F, the higher the trinuclear moiety-content based on the resin from which the binuclear moiety-content is subtracted.

The acid catalyst used in step 1 may be a fixed bed of a solid acid catalyst such as a cation-exchange resin; and organic and inorganic acids such as hydrochloric acid, sulfuric acid, salicylic acid, p-toluenesulfonic acid and oxalic acid.

The reaction temperature and period vary depending on various factors such as the kinds and the amounts of the acid catalysts used and the reaction molar ratio: P/F, but in general range from 50° to 110° C. and 0.5 to 10 hours, respectively.

When a catalyst such as a cation-exchange resin is used in a fixed bed, it is not necessary to remove the catalyst from the reaction product after completion of the reaction, while the unreacted formaldehyde, the water formed during the reaction or the like are removed by, for instance, distillation under reduced pressure. On the other hand, when an inorganic acid such as hydrochloric acid or oxalic acid is used, the acid catalyst is removed after the reaction simultaneously with the unreacted formaldehyde and added and generated water through, for instance, distillation under reduced pressure.

Then the unreacted phenol is removed by, for instance, distillation under reduced pressure. These separation and removal steps may be carried out separately, or a partial condenser and a complete condenser are used in combination to remove phenol through partial condensation in the partial condenser and to subsequently condense water or the like by the complete condenser. The phenol thus recovered can of course be reused as a starting material.

The binuclear moiety-content of the crude bisphenol F 2 thus prepared in step 1 is, for instance, 68% by weight for P/F of 6, 78% by weight for P/F of 10 and 87% by weight for P/F of 20 when oxalic acid is used as the acid catalyst.

The crude bisphenol F 2 thus obtained is then supplied to distillation step 4.

Stills usable in the distillation step of the present invention are preferably those equipped with a partial condenser capable of condensing a part of evaporated gases discharged from the still and of returning the condensed liquid to the still and the stills preferably used in the invention are, for instance, a falling film evaporator and a centrifugal-film evaporator.

If a plurality of stills are employed, each still may or may not be equipped with a partial condenser, but at least a still used in the final stage is preferably provided with a partial condenser. In this case, the stills of the foregoing types are preferably used.

In the method of the invention, the use of a distillation temperature of higher than 250° C. is sometimes accompanied by decomposition and/or coloration of bisphenol F. On the other hand, if the temperature is less than 200° C., the pressure must be reduced to less than 1 mm Hg.

In the distillation step of the present invention, for instance, the crude bisphenol F is continuously fed to a distillation apparatus equipped with a still, a partial condenser and a complete condenser, followed by distillation of the crude bisphenol F at a pressure of 1 to 5 mm Hg and a temperature of 220° to 250° C. while a part of the gas discharged from the still is condensed in the partial condenser, the condensed liquid is returned to the still and the remaining part of the generated gas is condensed in the complete condenser to thus continuously give highly pure bisphenol F as a distillate and to continuously withdraw a still-bottom product.

Alternatively, the distillation step may likewise be performed by, for instance, the following manner using three stills.

In this method, the crude bisphenol F is continuously fed to the first still to distill it at a pressure of 1 to 5 mm Hg and a temperature of 200° to 250° C. and the entire gas generated in the first still is fed to the complete condenser; or the crude bisphenol F is distilled while a part of the generated gas is condensed in the partial condenser, the condensed liquid is returned to the first still and the other part of the gas is introduced into the complete condenser, and simultaneously the still-bottom product from the first still is continuously supplied to the second still. In the second still, the still-bottom product is distilled in the same manner used in the first still and the second still-bottom product is continuously fed to the third still. In the third still, the distillation is carried out at the same pressure and a temperature preferably ranging from 220° to 250° C. while a part of the generated gas is condensed in the partial condenser, the condensed liquid is re-turned to the third still and the other part of the gas is introduced into the complete condenser. At the same time, the third still-bottom product is continuously withdrawn from the third still. The complete condenser collectively condenses all of the non-condensed gases discharged from these three stages to thus continuously produce highly pure bisphenol F as a distillate.

The partial condensation ratio of the foregoing partial condenser, i.e., the weight ratio of the condensed liquid to the non-condensed gases in general ranges from 0.05 to 0.5. If it is less than 0.05, the binuclear moiety-content of the distillate is less than 98% by weight in order to limit the binuclear moiety-content of the still-bottom product to not more than 15% by area, while if it exceeds 0.5, the use of a superfluous energy would be required.

The binuclear moiety-content of the distillate can easily be controlled to not less than 98% by weight, even when the binuclear moiety-content of the still-bottom product is not more than 15% by area by returning the partially condensed liquid to the still using such a partial condenser.

When a plurality of stills are used, it is preferred to control the binuclear moiety-content of the liquid feed supplied to the final still to not less than 30% by area. This is because if it is less than 30% by area, the combined distillates from all of the stills often have a binuclear moiety-content of less than 98% by weight even if the distillate from the final still has an extremely high binuclear moiety-content.

The complete condenser preferably used in the invention may be, for instance, a multi-tubular cylindrical heat exchanger and a coil heat exchanger. In addition, the partial condenser usable in the present invention may be, for instance, a multi-tubular cylindrical heat exchanger and a coil heat exchanger. Moreover, these condensers may be one in which the distillation line extending from the still to the complete condenser can externally be cooled.

The still-bottom product withdrawn from the distillation step according to the present invention has a binuclear moiety-content of from 1 to 15% by area and preferably 1 to 10% by area. If it exceeds 15% by area, the yield of the useful binuclear moieties is reduced, while if it is less than 1% by area, the distillation requires the use of a high temperature and this becomes a cause of problems of, for instance, decomposition and coloration of the distillate or still-bottom product.

Another merit of the present invention is to be able to form a still-bottom product which can be used as a useful novolak phenol resin having a low binuclear moiety-content, by adjusting the binuclear moiety-content of the still-bottom product to not more than 15% by area, preferably not more than 10% by area. In addition, the still-bottom product can be polymerized through polycondensation with formaldehyde to give a high molecular weight novolak phenol resin having a low binuclear moiety-content.

The distillation of the crude bisphenol F 2 under the foregoing conditions for distillation allows the formation of high molecular weight bisphenol F 6 in the form of a distillate 5 and novolak phenol resin 10 having a low binuclear moiety-content as a still-bottom product. If the temperature and pressure are appropriately selected so that they fall within the corresponding ranges defined above, the binuclear moiety-contents in the still-bottom product and the distillate 5 can be limited to not more than 15% by area and not less than 95% by weight, respectively. If the binuclear moiety-content in the still-bottom product exceeds 15% by area, the still-bottom product is in the form of paste and this makes the handling thereof quite difficult. Moreover, the use thereof as a material for epoxy resin or as a hardener causes problems of formation of flashes on the resulting molded articles and of reduction in strength of the articles. On the other hand, if the binuclear moiety-content in the distillate 5 is less than 95% by weight, the use of the distillate as a material for preparing epoxy resins adversely affects the corrosion resistance and resistance to chemicals of the resulting epoxy resins.

Novolak phenol resin 10 containing a small amount of the binuclear moieties is withdrawn from the still as the still-bottom product, allowed to cool in the air or forced to cool to a temperature of about 40° C. or lower and then preferably pulverized into fine powder to give novolak phenol resin 10 having a low binuclear moiety-content. The method for pulverization is not restricted to a specific one and pulverizers preferably used include, for instance, a ball mill and a jet mill.

If bisphenol F for general use and a novolak phenol resin having a low binuclear moiety-content are simultaneously prepared according to the second embodiment of the present invention, the molar ratio of phenol to formaldehyde: P/F in general ranges from 6 to 20 and the resulting crude bisphenol F 2 is divided into two portions (crude bisphenol F 3 and crude bisphenol F 9) in a proper ratio. Crude bisphenol F 3 is fed to distillation step 4 and distilled. The distillate 5 formed therein is transferred to mixing step 7. On the other hand, crude bisphenol F 9 is directly fed to mixing step 7 and mixed with distillate 5 to give bisphenol F 8 for general use comprising the binuclear moieties in an amount ranging from 88 to 93% by weight. The mixing apparatus used in this step is not restricted to a specific one and any mixing apparatus used for admixing liquids can be used. Examples thereof include a vessel equipped with a stirring machine and a static mixer.

For instance, if the reaction of phenol with formaldehyde is performed at a P/F of 10 to give bisphenol F for general use having a binuclear moiety-content of 91% by weight, the foregoing divisional ratio (weight ratio: crude bisphenol F 3/crude bisphenol F 9) is set at about 68:32. At the same time, novolak phenol resin 10 having a low binuclear moiety-content is formed, as the still-bottom product from distillation step 4, in an amount of about 18% by weight on the basis of bisphenol F for general use. The binuclear moiety-contempt of this still-bottom product is preferably not more than 15% by area and in particular not more than 10% by area.

Highly pure bisphenol F 6 and bisphenol F 8 for general use can of course be simultaneously prepared even when the divisional ratio is increased. Highly pure bisphenol F 6 and bisphenol F 8 for general use may be stored in the form of liquids while applying heat or may be pulverized in a separate granulation step to give granular products.

If highly pure bisphenol F 6, bisphenol F 8 for general use and novolak phenol resin 10 having a low binuclear moiety-content are simultaneously prepared according to the third embodiment of the present invention, the same procedures used in the practice of the second embodiment may be adopted except that a part of highly pure bisphenol F prepared in the same manner used in the second embodiment is admixed with the remaining crude bisphenol F to give bisphenol F for general use.

The method will be explained hereinafter for simultaneously preparing highly pure bisphenol F 6 and/or bisphenol F 8 for general use and novolak phenol resin 10 having a low binuclear moiety-content and/or high molecular weight novolak phenol resin 12 having a low binuclear moiety-content according to the fourth embodiment of the present invention.

In this fourth embodiment, highly pure bisphenol F 6, bisphenol F 8 for general use and novolak phenol resin 10 having a low binuclear moiety-content are prepared in the same manner used in the first, second or third embodiment.

At least a part of the resulting novolak phenol resin 10 having a low binuclear moiety-content is fed to polymerization step 11. The polymerization performed in step 11 for the preparation of high molecular weight novolak phenol resin 12 is carried out in the following manner.

To a reactor used in step 11, there are charged novolak phenol resin 10 having a low binuclear moiety-content, formaldehyde and a catalyst and they are reacted at a temperature generally ranging from 50° to 110° C. for 0.5 to 10 hours with stirring.

Examples of the formaldehyde component include formalin, paraformaldehyde, hexamethylenetetramine, trioxan and cyclic formal.

The catalyst usable in this reaction may be, for instance, inorganic acids such as hydrochloric acid and sulfuric acid; and organic acids such as salicylic acid, p-toluenesulfonic acid and oxalic acid.

The resulting reaction product is heated to remove the remaining catalyst, the unreacted formaldehyde and the water generated during the reaction to give high molecular weight novolak phenol resin 12 having a low binuclear moiety-content. This high molecular weight novolak phenol resin 12 is withdrawn from the reactor and then allowed to cool in the air or forced to cool to a temperature of about 40° C. or lower and then preferably pulverized into fine powder. The method for pulverization is not restricted to a specific one and pulverizers preferably used include, for instance, a ball mill and a jet mill.

The novolak phenol resin of the present invention has a low binuclear moiety-content and preferably has a high trinuclear moiety-content. The trinuclear moiety-content thereof is adjusted to not less than 50% by area and the content of the sum of the trinuclear and tetranuclear moieties is adjusted to not less than 80% by area on the basis of the resin from which the binuclear or lower moieties are subtracted, whereby the resin provides a high molecular weight novolak resin having a sufficiently low viscosity.

In the polymerization, the weight ratio of novolak phenol resin 10 having a low binuclear moiety-content to formaldehyde (hereinafter referred to as "N/F") is preferably not less than 15. This is because if the ratio: N/F is less than 15, the softening point of the resulting high molecular weight novolak resin exceeds 120° C. This impairs the flow properties thereof and makes the handling thereof difficult when it is used as, for instance, a molding material.

The binuclear moiety-content of the high molecular weight novolak phenol resin prepared according to such a method falls within the range of from about 3 to 6% by area. In this respect, the binuclear moiety-content of novolak phenol resins conventionally used as hardeners for epoxy resins, for instance, falls within the range of from 18 to 23% by area, when they are formed so that the softening points thereof are 80° C. and falls within the range of from 6 to 9% by area when they are formed so that the softening points thereof are 120° C. Therefore, the binuclear moiety-content of the resin of the present invention is substantially low as compared with that of these conventional resins. Moreover, the weight-average molecular weight (Mw) thereof ranges from 340 to 1600 and the number-average molecular weight (Mn) thereof ranges from 300 to 800. Thus, the parameter Mw/Mn indicating the poly-dispersity of the molecules ranges from about 1.2 to about 2.5. This means that the molecular weight distribution of the resin is narrow.

One of characteristic properties of the present invention is that the production ratio between highly pure bisphenol F 6 and/or bisphenol F 8 for general use and novolak phenol resin 10 having a low binuclear moiety-content and/or high molecular weight novolak phenol resin 12 having a low binuclear moiety-content can be controlled by adjusting the reaction molar ratio: P/F in step 1 and, therefore, the present invention can cope with various demands.

The epoxy resin used in the composition of the present invention as an essential component carries at least two epoxy groups in the molecule. Examples of such epoxy resins are phenol novolak epoxy resins, o-cresol novolak epoxy resins, phenol aralkyl epoxy resins, bisphenol A epoxy resins, bisphenol F epoxy resins, and brominated bisphenol A epoxy resins and brominated bisphenol F epoxy resins to which flame retardancy is imparted. Moreover, these epoxy resins may be liquid epoxy resins. The use of such a liquid epoxy resin permits further reduction in the viscosity of the resulting composition. These epoxy resins may be used alone or in any combination.

The novolak phenol resin as another essential component of the epoxy resin composition according to the present invention is, in particular, characterized by such distribution of nuclear numbers of moieties that the binuclear moiety-content is low, while the trinuclear moiety-content is high. The novolak phenol resin having such a characteristic distribution of nuclear numbers of moieties has a low content of binuclear moieties which do not take part in the crosslinking reaction and, therefore, the cured product thereof has a high degree of crosslinking and improved heat resistance. The reduction of the binuclear moiety-content results in an increase in the viscosity of the resulting resin as compared with a resin having a high binuclear moiety-content, but the resin used in the invention has a high trinuclear moiety-content and accordingly, the resin has a low melt viscosity which has never been achieved through the use of other novolak phenol resins having glass transition points (hereinafter referred to as "Tg") on curing identical to that of the cured resin used in the invention.

The binuclear moiety-content of the novolak phenol resin used in the composition of the invention as an essential component is in general not more than 10% by weight. The binuclear moieties do not contribute to the crosslinking reaction and thus the content thereof is preferably low, while if the content of binuclear moieties is increased, the viscosity of the resin is conversely lowered. For this reason, the novolak phenol resins used in the invention may comprise binuclear moieties to such an extent that the presence thereof does not adversely affect the degree of crosslinking required for the composition.

The novolak phenol resin used in the invention has a tetranuclear moiety-content ranging from 5 to 15% by weight.

The trinuclear moiety-content of the novolak phenol resin is 2 to 19 times the tetranuclear moiety-content.

The novolak phenol resins should have low melt viscosities as compared with other resins which can provide cured products having glass transition points (Tg) identical to that of the cured novolak phenol resin used in the invention as long as they have the distribution of nuclear numbers of moieties, which satisfies the foregoing requirements.

The epoxy resins composition according to the present invention which comprises a novolak phenol resin and an epoxy resin as essential components may optionally comprise other components such as other phenolic resins, hardening-promoting agents and/or a variety of additives in such amounts that the intended purposes of the present invention are not impaired.

The epoxy resin composition of the present invention may further comprise a compound which can promote the reaction of the epoxy groups of the epoxy resin with the hydroxyl groups of the hardener. Examples of hardening-promoting agents include nitrogen atom-containing compounds, phosphines and onium salts.

In the epoxy resin composition according to the present invention, the epoxy resin and the novolak phenol resin are mixed in a ratio such that the amount of hydroxyl groups of the novolak phenol resin in general ranges from 0.1 to 10 moles per mole of epoxy group of the epoxy resin.

The present invention will hereinafter be explained in more detail with reference to the following working Examples and Comparative Examples. In the following Examples and Comparative Examples, the determination and evaluation of various characteristic properties were carried out in the following methods (1) to (5).

(1) Determination of 4,4'-moiety, 2,4'-moiety and 2,2'-moiety present in highly pure bisphenol F and bisphenol F for general use: The amount of these moieties were determined by liquid chromatography (column: Radial Pack C18 (trade name) available from Waters Company; eluent: acetonitrile/water (with gradient)). The results are expressed in terms of "% by weight of the sum of the foregoing three binuclear moieties" according to the internal standard method.

(2) Determination of the content of each moiety present in each corresponding novolak phenol resin or high molecular weight novolak phenol resin: The content of each moiety is expressed in terms of "% by area" as determined by gel permeation chromatography (two columns: G4000HXL×2+G2500HXL+G2000HXL (trade name) available from Tosoh Corporation; eluent: tetrahydrofuran). The average molecular weight was calculated by setting each peak determined in the same manner in correspondence to the molecular weight it. proportion to the number of phenol nucleus.

(3) Viscosity: The viscosity was determined using ICI Cone & Plate Type Viscometer (available from Research Equipment Company, London) at 130° C. for still-bottom products and 150° C. for high molecular weight novolak phenol resins.

(4) Glass Transition Temperature (Tg): This was determined according to TMA (Thermomechanical Analysis) method.

(5) Softening Point: This was determined according to the method defined in JIS K-2207.

Preparation of Hardened Epoxy Products

There were dissolved, in a minimal amount of acetone, each of the still-bottom products obtained in Examples 5 to 8 and 14 to 16 and Comparative Examples 6 to 7 as a hardener, a base resin and a catalyst and the resulting solution was formed into a cast sheet having a thickness of about 3 mm which was used for the determination of various properties. The amount of the hardener and the catalyst used were 49 parts by weight and 1 part by weight respectively per 100 parts by weight of the base resin. The base resin used was an epoxy resin (EOCN-102S having an epoxy equivalent of 214, a softening point of 75.0° C. and a viscosity of 6.3 P (at 150° C. ), available from Nippon Kayaku Co., Ltd. ). The catalyst used was triphenylphosphine (TPP).

Example 1

To an agitated vessel type reactor of stainless steel equipped with a stirring machine, a temperature control device, a reflux condenser, a complete condenser and a pressure reducing device, there were continuously fed a phenol solution prepared by dissolving oxalic acid dihydrate in an amount of 0.046% by weight based on the amount of phenol and 47% formalin while adjusting the molar ratio: phenol/formaldehyde (P/F) to 20 and the flow rate of the sum of these solution supplied to 360 kg/hr.

The reaction was carried out at a reaction temperature of 70° C. and a residence time of 4 hours, followed by continuously withdrawing the reaction mixture and continuously feeding it to a packed distillation column in which the water and the unreacted materials were removed by heating the mixture at 170° C. and a pressure of 20 mm Hg to thus give crude bisphenol F.

The resulting crude bisphenol F comprised 28.9% by weight of 4,4'-moiety, 38.2% by weight of 2,4'-moiety and 10.9% by weight of 2,2'-moiety (total amount of these binuclear moieties was 78.0% by weight).

This crude bisphenol F was continuously fed, at a flow rate of 30 kg/hr, to a centrifugal-film evaporator operated at a pressure of 3 mm Hg and simultaneously the distillate and still-bottom product formed therein were continuously withdrawn from the evaporator. The centrifugal-film evaporator used was equipped with a jacket in which a heating medium was circulated. Moreover, the centrifugal-film evaporator was equipped with a coil heat exchanger as a partial condenser and cooling water was circulated in the coil of the partial condenser to adjust the partial condensation ratio (weight ratio) in such a manner that a part of the gas generated in the evaporator was condensed therein and returned to the evaporator.

When the amount of the heating medium was adjusted so that the temperature of the still-bottom product was set at 245° C., while the amount of the cooling water was controlled so that the partial condensation ratio was equal to 0.2, the binuclear moiety-content of the still-bottom product was 6% by weight and that of the distillate was 98% by weight. Thus, a highly pure bisphenol F having a binuclear moiety-content of 98% by weight was obtained. No coloration of the resulting highly pure bisphenol F was observed.

Example 2

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product formed therein were likewise continuously withdrawn from the evaporator. The centrifugal-film evaporator used was equipped with a jacket in which a heating medium was circulated. Moreover, the centrifugal-film evaporator was further equipped with a coil heat exchanger as a partial condenser so that a part of the gas generated in the evaporator was condensed therein and returned to the evaporator.

The cooling water was circulated in the coil of the partial condenser to adjust the partial condensation ratio (weight ratio). When the amount of the heating medium was adjusted so that the temperature of the still-bottom product was set at 240° C., while the amount of the cooling water was controlled so that the partial condensation ratio was equal to 0.2, the binuclear moiety-content of the still-bottom product was 10% by weight and that of the distillate was 99% by weight. Thus, a highly pure bisphenol F having a binuclear moiety-content of 99% by weight was obtained. No coloration of the resulting highly pure bisphenol F was observed.

Example 3

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product formed therein were likewise continuously withdrawn from the evaporator. The centrifugal-film evaporator used was equipped with a jacket in which a heating medium was circulated. Moreover, the centrifugal-film evaporator was further equipped with a coil heat exchanger as a partial condenser so that a part of the gas generated in the evaporator was condensed therein and returned to the evaporator.

The cooling water was circulated in the coil of the partial condenser to adjust the partial condensation ratio (weight ratio). When the amount of the heating medium was adjusted so that the temperature of the still-bottom product was set at 240° C., while the amount of the cooling water was controlled so that the partial condensation ratio was equal to 0.1, the binuclear moiety-content of the still-bottom product was 10% by weight and that of the distillate was 98.4% by weight. Thus, a highly pure bisphenol F having a binuclear moiety-content of 98.4% by weight was obtained. No coloration of the resulting highly pure bisphenol F was observed.

Example 4

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a first centrifugal-film evaporator operated at a pressure of 3 mm Hg and simultaneously the distillate and still-bottom product were likewise continuously withdrawn from the evaporator. The still-bottom product had a binuclear moiety-content of 50% by weight. This still-bottom product was fed to a second centrifugal-film evaporator operated at a pressure of 3 mm Hg and simultaneously the distillate and still-bottom product were likewise continuously withdrawn from the evaporator. The distillates from the first and second evaporators were mixed and then withdrawn.

These two centrifugal-film evaporators used each were equipped with a jacket in which a heating medium was circulated. Moreover, the second centrifugal-film evaporator was further equipped with a coil heat exchanger as a partial condenser so that a part of the gas generated in the evaporator was condensed therein and returned to the evaporator.

The cooling water was circulated in the coil of the partial condenser to adjust the partial condensation ratio (weight ratio). When the amounts of the heating mediums were adjusted so that the temperatures of the still-bottom products from the first and second evaporators were set at 227° C. and 240° C. respectively, while the amount of the cooling water was controlled so that the partial condensation ratio in the second evaporator was equal to 0.2, the binuclear moiety-content of the still-bottom product from the second evaporator was 10% by weight and that of the combined distillate (mixed distillates from the first and second evaporators) was 99.3% by weight. Thus, a highly pure bisphenol F having a binuclear moiety-content of 99.3% by weight was obtained. No coloration of the resulting highly pure bisphenol F was observed.

Comparative Example 1

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product were likewise continuously withdrawn from the evaporator. The centrifugal-film evaporator used was equipped with a jacket in which a heating medium was circulated. When the amount of the heating medium was adjusted so that the temperature of the still-bottom product was set at 245° C., the binuclear moiety-content of the still-bottom product was 6% by weight and that of the distillate was 84% by weight. Thus, a bisphenol F having a binuclear moiety-content of 84% by weight was obtained.

Comparative Example 2

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product were likewise continuously withdrawn from the evaporator. The centrifugal-film evaporator used was equipped with a jacket in which a heating medium was circulated. When the amount of the heating medium was adjusted so that the temperature of the still-bottom product was set at 240° C., the binuclear moiety-content of the still-bottom product was 10% by weight and that of the distillate was 89.5% by weight. Thus, a bisphenol F having a binuclear moiety-content of 89.5% by weight was obtained.

Comparative Example 3

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product were likewise continuously withdrawn from the evaporator. The centrifugal-film evaporator used was equipped with a jacket in which a heating medium was circulated. When the amount of the heating medium was adjusted so that the temperature of the still-bottom product was set at 230° C., the binuclear moiety-content of the still-bottom product was 30% by weight and that of the distillate was 98% by weight. Thus, a highly pure bisphenol F having a binuclear moiety-content of 98% by weight was obtained.

The resulting bisphenol F had a high purity, but a large amount of useful binuclear moieties remained in the still-bottom product. Thus this method for preparing highly pure bisphenol F is insufficient in efficiency.

Comparative Example 4

A crude bisphenol F was prepared in the same manner used in Example 1. The resulting crude bisphenol F had a composition identical to that of the crude bisphenol F obtained in Example 1.

This crude bisphenol F was continuously fed, at a flow rate of 30 kg/hr, to a centrifugal-film evaporator operated at a pressure of 3 mm Hg and simultaneously the distillate and still-bottom product were likewise continuously withdrawn from the evaporator. The centrifugal-film evaporator used was equipped with a jacket in which a heating medium was circulated. When the amount of the heating medium was adjusted so that the temperature of the still-bottom product was set at 227° C., the binuclear moiety-content of the still-bottom product was 50% by weight and that of the distillate was 99.4% by weight. Thus, a highly pure bisphenol F having a binuclear moiety-content of 99.4% by weight was obtained.

The resulting bisphenol F had a high purity, but a large amount of useful binuclear moieties remained in the still-bottom product. Thus this method for preparing highly pure bisphenol F is insufficient in efficiency.

Comparative Example 5

A crude bisphenol F was prepared in the same manner used in Example 1. The resulting crude bisphenol F had a composition identical to that of the crude bisphenol F obtained in Example 1.

This crude bisphenol F was fed, at a flow rate of 110 kg/hr, to a rectifying column equipped with ten perforated plates (ten-stage) and operated at a column head-pressure of 3 mm Hg and simultaneously the distillate and the column-bottom product were likewise continuously withdrawn therefrom. This column was provided with a complete condenser on the column head and the reflux ratio was controlled to 0.2 by an electromagnetic valve capable of opening and closing through the control of a timer. The temperature of the bottom of the column was adjusted by a heating medium.

An attempt was made to adjust the temperature of the bottom of the column in such a manner that the binuclear moiety-content of the bottom product was set at 10% by weight, but the temperature exceeded 260° C., the bisphenol F was decomposed into phenol and this resulted in an increase of the column head-pressure. Accordingly, the column could not be operated stably.

Example 5

To a 3000 ml volume reactor of stainless steel equipped with a stirring machine, a temperature control device, a reflux condenser, a complete condenser and a pressure reducing device, there were fed 2000 g of phenol, 287.5 g of 37% formalin (P/F=6) and 5.6 g of oxalic acid dihydrate. The contents were reacted under atmospheric pressure by heating to 70° C. over 4 hours with stirring while operating the reflux condenser.

Then the reaction product thus obtained was heated to 160° C. under atmospheric pressure to remove the water and a small amount of phenol and further heated at a pressure of 20 mm Hg till the temperature reached to 170° C. to remove unreacted phenol. Then the product was heated at 210° C. and a pressure of 6 mm Hg to further remove the remaining unreacted phenol to give 640 g of a crude bisphenol F.

The resulting crude bisphenol F comprised 26.5% by weight of 4,4'-moiety, 32.6% by weight of 2,4'-moiety and 8.9% by weight of 2,2'-moiety (total amount of these binuclear moieties was 68.0% by weight).

This crude bisphenol F was distilled using an apparatus equipped with McMahon packing having a diameter of 15 mm and a height of 20 mm as Demister (trade name). The distillation was carried out at a pressure of 3 mm Hg till the final temperature reached 250° C. to give 440 g of a highly pure bisphenol F as a distillate and 198 g of a novolak phenol resin having a low binuclear moiety-content as a bottom product. The bottom product was cooled to room temperature through air-cooling to give a solid product capable of being pulverized.

Figure 3:
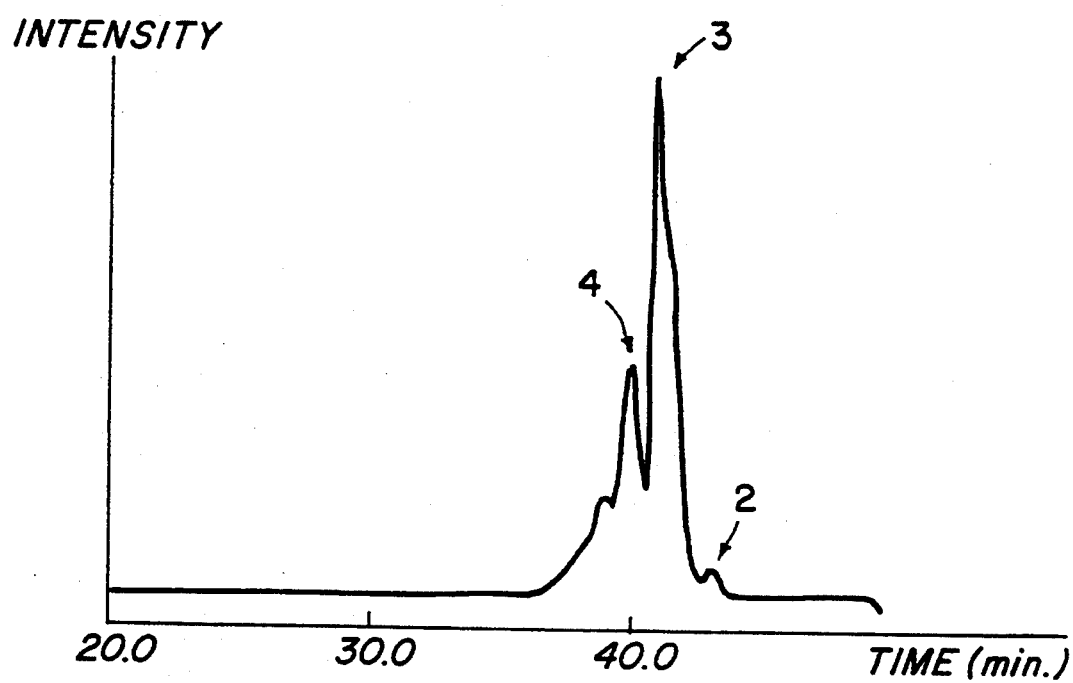
FIG. 3 is a chart showing the distribution of nuclear numbers of moieties present in the phenol resin prepared in Example 5.

The composition of the resulting highly pure bisphenol F is listed in the following Table 1 and the binuclear moiety-content, molecular weight, softening point and viscosity of the resulting novolak phenol resin having a low binuclear moiety-content are summarized in the following Table 2. In addition, the binuclear moiety-content, the trinuclear moiety-content calculated based on the amount of the bottom product from which the binuclear moiety-content was subtracted, the content of the sum of the trinuclear and tetranuclear moieties and viscosity of the bottom product as well as Tg of the hardened epoxy product are summarized in the following Table 3. An analytical chart showing the distribution of nuclear numbers of moieties present in the novolak phenol resin prepared herein is shown in FIG. 3.

Example 6

There were mixed 2000 g of phenol and 172.5 g of 37% formalin (P/F=10) and then 5.6 g of oxalic acid dihydrate was added to the mixture, followed by reacting the mixture with heating at 70° C. for 4 hours. Then the reaction system thus obtained was heated to 160° C. under atmospheric pressure to remove the water and a small amount of phenol and further heated at a pressure of 20 mm Hg till the temperature reached 170° C. to remove unreacted phenol. Then the product was heated at 210° C. and a pressure of 6 mm Hg to further remove the remaining unreacted phenol to give 350 g of a crude bisphenol F.

The resulting crude bisphenol F comprised 28.9% by weight of 4,4'-moiety, 38.2% by weight of 2,4'-moiety and 10.9% by weight of 2,2'-moiety (total amount of these binuclear moieties was 78.0% by weight).

This crude bisphenol F was distilled using an apparatus equipped with McMahon packing having a diameter of 15 mm and a height of 20 mm. The distillation was carried out at a pressure of 3 mm Hg till the final temperature reached 245° C. to give 270 g of a highly pure bisphenol F and 79 g of a bottom product. The bottom product was cooled to room temperature to give a solid product capable of pulverization.

Figure 4:
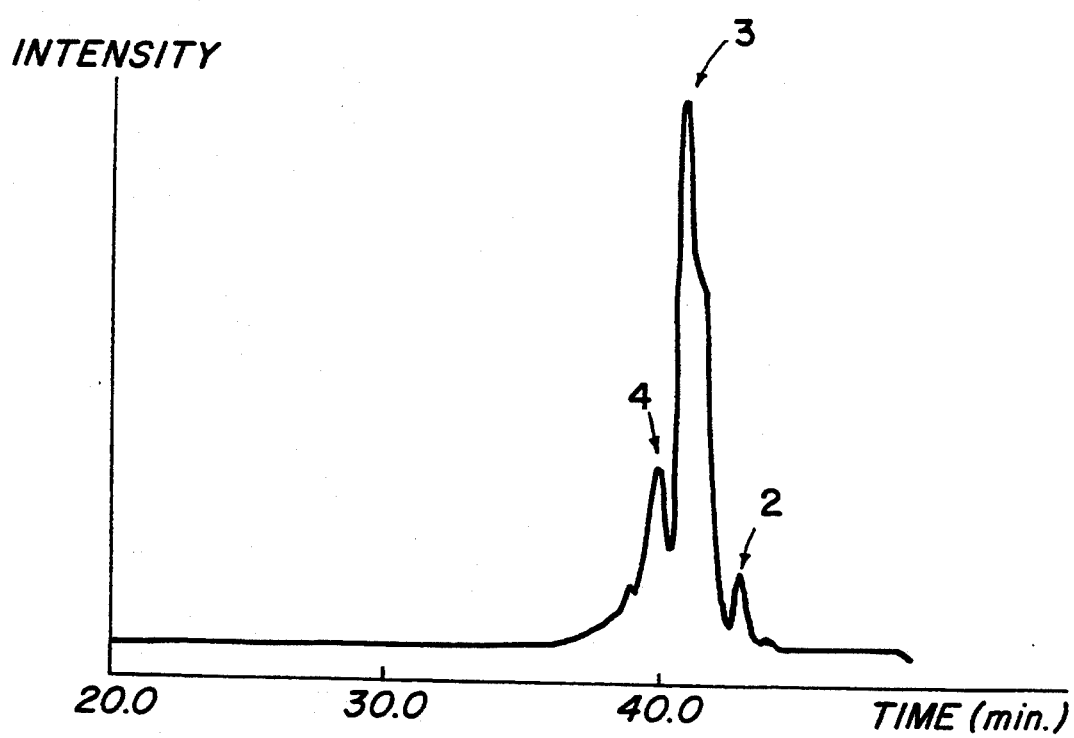
FIG. 4 is a chart showing the distribution of nuclear numbers of moieties present in the phenol resin prepared in Example 6.

The composition of the resulting highly pure bisphenol F is listed in Table 1 and the binuclear moiety-content, molecular weight, softening point and viscosity of the resulting bottom product are summarized in Table 2. In addition, the binuclear moiety-content, the trinuclear moiety-content calculated based on the amount of the bottom product from which the binuclear moiety-content was subtracted, the content of the sum of the trinuclear and tetranuclear moieties and viscosity of the bottom product as well as Tg of the hardened epoxy product are summarized in Table 3. An analytical chart showing the distribution of nuclear numbers of moieties present in the novolak phenol resin prepared in this Example is shown in FIG. 4.

Example 7

The same procedures used in Example 5 were repeated to give 200 g of a crude bisphenol F except that a mixture of 2000 g of phenol and 86.3 g of 37% formalin (P/F=20).

The resulting crude bisphenol F comprised 28.7% by weight of 4,4'-moiety, 43.5% by weight of 2,4'-moiety and 14.8% by weight of 2,2'-moiety (total amount of these binuclear moieties was 87.0% by weight).

This crude bisphenol F was distilled using an apparatus identical to that used in Example 5 at a pressure of 3 mm Hg till the final temperature reached 245° C. to give 171 g of a highly pure bisphenol F and 27 g of a bottom product. The bottom product was cooled to room temperature to give a solid product capable of pulverization.

The composition of the resulting highly pure bisphenol F is listed in Table 1 and the binuclear moiety-content, molecular weight, softening point and viscosity of the resulting bottom product are summarized in Table 2. In addition, the binuclear moiety-content, the trinuclear moiety-content calculated based on the amount of the bottom product from which the binuclear moiety-content was subtracted, the content of the sum of the trinuclear and tetranuclear moieties and viscosity of the bottom product as well as Tg of the hardened epoxy product are summarized in Table 3.

Example 8

The same procedures used in Example 5 were repeated to give a crude bisphenol F except that a mixture of 2000 g of phenol and 57.5 g of 37% formalin (P/F=30).

This crude bisphenol F was distilled using an apparatus identical to that used in Example 5 at a pressure of 3 mm Hg till the final temperature reached to 240° C. to give 13 g of a bottom product. The bottom product was cooled to room temperature to give a solid product capable of pulverization.

Figure 5:
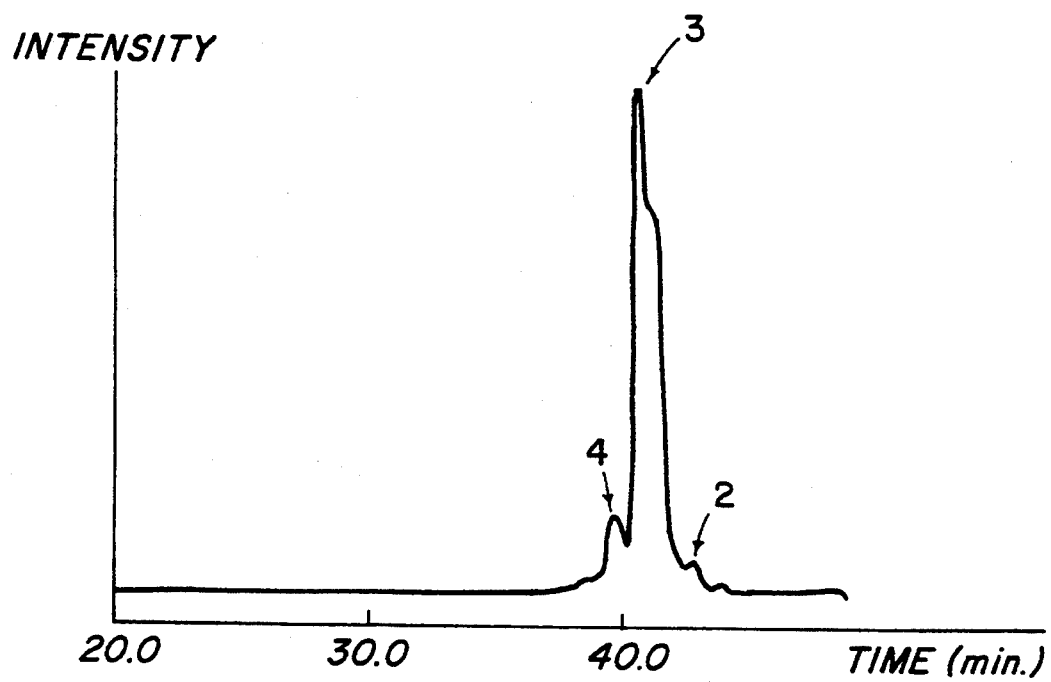
FIG. 5 is a chart showing the distribution of nuclear numbers of moieties present in the phenol resin prepared in Example 8.

The composition of the resulting highly pure bisphenol F is listed in Table 1 and the binuclear moiety-content, molecular weight, softening point and viscosity of the resulting bottom product are summarized in Table 2. In addition, the binuclear moiety-content, the trinuclear moiety-content calculated based on the amount of the bottom product from which the binuclear moiety-content was subtracted, the content of the sum of the trinuclear and tetranuclear moieties and viscosity of the bottom product as well as Tg of the hardened epoxy product are summarized in Table 3. An analytical chart showing the distribution of nuclear numbers of moieties present in the novolak phenol resin prepared in this Example is shown in FIG. 5.

Comparative Example 6

The same procedures used in Example 5 were repeated to give a crude bisphenol F except that a mixture of 2000 g of phenol and 172.5 g of 37% formalin (P/F=10/1) was used.

This crude bisphenol F was distilled using an apparatus identical to that used in Example 5 at a pressure of 3 mm Hg till the final temperature reached 220° C. to give 97 g of a bottom product. The bottom product was cooled to room temperature to give a pasty solid incapable of pulverization.

Figure 6:
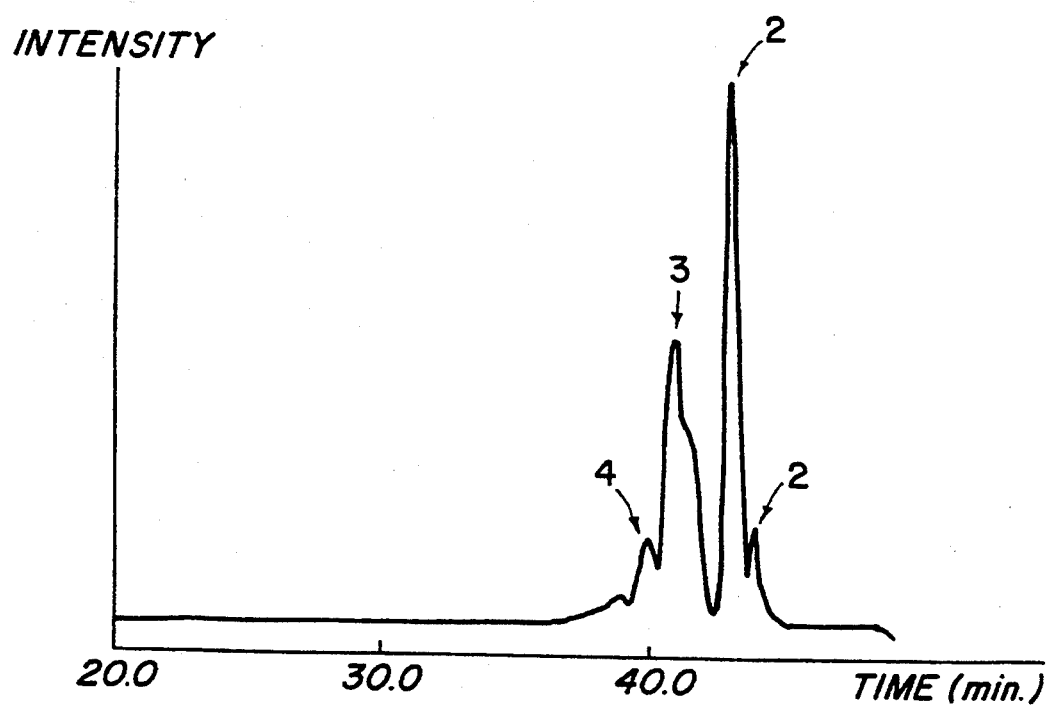
FIG. 6 is a chart showing the distribution of nuclear numbers of moieties present in the phenol resin prepared in Comparative Example 6.

The binuclear moiety-content, the trinuclear moiety-content calculated based on the amount of the bottom product from which the binuclear moiety-content was subtracted, the content of the sum of the trinuclear and tetranuclear moieties and viscosity of the bottom product as well as Tg of the hardened epoxy product are summarized in Table 3. An analytical chart showing the distribution of nuclear numbers of moieties present in the novolak phenol resin prepared in this Example is shown in FIG. 6.

Example 9

The same procedures used in Example 6 were repeated to give 260 g of a highly pure bisphenol F and 89 g of a bottom product except that the final temperature for the distillation was set at 237° C. The bottom product was cooled to room temperature to give a pasty product incapable of pulverization.

The composition of the resulting highly pure bisphenol F is listed in Table 1 and the binuclear moiety-content, molecular weight, softening point and viscosity of the resulting bottom product are summarized in Table 2.

Example 10

A crude bisphenol F (200 g) was prepared under the same conditions used in Example 5. This crude bisphenol F (170 g) was distilled under the same conditions used in Example 5 to give 17 g of a highly pure bisphenol F and 52 g of a bottom product. The bottom product was cooled to room temperature to give a solid product capable of pulverization.

The remaining crude bisphenol F (30 g) was mixed with the resulting highly pure bisphenol F (117 g) to give bisphenol F (147 g) for general use having a binuclear moiety-content of 91% by weight.

The composition of the resulting bisphenol F for general use is listed in Table 1 and the binuclear moiety-content, molecular weight, softening point and viscosity of the resulting bottom product are summarized in Table 2.

Example 11

A crude bisphenol F (200 g) was prepared under the same conditions used in Example 6. This crude bisphenol F (135.6 g) was distilled under the same conditions used in Example 6 to give 104 g of a highly pure bisphenol F and 30 g of a bottom product. The bottom product was cooled to room temperature to give a solid product capable of pulverization.

The remaining crude bisphenol F (64.4 g) was mixed with the resulting highly pure bisphenol F (104 g) to give bisphenol F (168.4 g) for general use having a binuclear moiety-content of 91% by weight.

The composition of the resulting bisphenol F for general use is listed in Table 1 and the binuclear moiety-content, molecular weight, softening point and viscosity of the resulting bottom product are summarized in Table 2.

Example 12

A crude bisphenol F (200 g) was prepared under the same conditions used in Example 7. This crude bisphenol F (70.8 g) was distilled under the same conditions used in Example 7 to give 60 g of a highly pure bisphenol F and 9 g of a bottom product. The bottom product was cooled to room temperature to give a solid product capable of pulverization.

The remaining crude bisphenol F (129.2 g) was mixed with the resulting highly pure bisphenol F (60 g) to give bisphenol F (189.2 g) for general use having a binuclear moiety-content of by weight.

The composition of the resulting bisphenol F for general use is listed in Table 1 and the binuclear moiety-content, molecular weight, softening point and viscosity of the resulting bottom product are summarized in Table 2.

TABLE 1

| Ex. No. | 4,4'-Moiety | 2,4'-Moiety | 2,2'-Moiety | B.M.-C |
|---|---|---|---|---|
| 5 | 37.4 | 46.8 | 12.7 | 96.9 |
| 6 | 34.5 | 48.9 | 15.6 | 99.0 |
| 7 | 32.4 | 50.1 | 17.0 | 99.5 |
| 8 | 32.4 | 50.1 | 17.0 | 99.5 |
| 9 | 36.0 | 49.5 | 14.1 | 99.6 |
| 10 | 35.2 | 43.9 | 11.9 | 91.0 |
| 11 | 33.4 | 44.8 | 12.8 | 91.0 |
| 12 | 29.9 | 45.6 | 15.5 | 91.0 |

Note:
The numerical value are expressed in terms of "% by weight".
B.M.-C: Binuclear Moiety-content.

TABLE 2

| Ex. No. | B.M.-C (wt %) | Mw | Mn | Variance (Mw/Mn) | Softening Point (°C.) | Viscosity (P, at 130° C.) |
|---|---|---|---|---|---|---|
| 5 | 4.0 | 340 | 318 | 1.07 | 65 | 1.1 |
| 6 | 7.1 | 325 | 307 | 1.06 | 63 | 1.0 |
| 7 | 7.2 | 310 | 295 | 1.05 | 62 | 0.9 |
| 8 | 7.0 | 308 | 292 | 1.05 | 61 | 0.6 |
| 9 | 16.0 | 308 | 290 | 1.06 | N.D. | 0.8 |
| 10 | 4.0 | 340 | 318 | 1.07 | 65 | 1.1 |
| 11 | 7.1 | 325 | 307 | 1.06 | 63 | 1.0 |
| 12 | 10.2 | 310 | 295 | 1.05 | 62 | 0.9 |

Note:
Mw: weight-average molecular weight
Mn: number-average molecular weight
N.D.: Determination thereof was impossible.

TABLE 3

| Ex. No. | 2-Nuclear Moiety-content | 3-Nuclear Moiety-content | Content of 2- + 3-Nuclear Moieties | Viscosity (P, at 130° C.) | Tg (°C.) |
|---|---|---|---|---|---|
| 5 | 4.0 | 59.2 | 88.5 | 1.1 | 171 |
| 6 | 7.1 | 72.7 | 92.3 | 0.9 | 169 |
| 7 | 7.2 | 84.0 | 95.0 | 0.8 | 168 |
| 8 | 7.0 | 87.7 | 98.0 | 0.6 | 168 |
| 6* | 24.1 | 62.2 | 86.5 | <0.1 | 149 |

*: Comparative Example
Note:
1) Contents are expressed in terms of "% by area".
2) Contents of 3-nuclear moieties and 3- + 4-nuclear moieties are calculated based on the amount of the resin from which the binuclear moiety-content is subtracted.

Example 13

The same procedures for reaction and distillation used in Example 5 were repeated to give 440 g of a highly pure bisphenol F as a distillate and 198 g of a novolak phenol resin having a low binuclear moiety-content as a bottom product. To the resulting bottom product, there were added 9.6% by weight of 37% formalin and 0.28% by weight of oxalic acid dihydrate and the mixture was reacted at 100° C. for 4 hours. Then the reaction mixture was heated at a pressure of 200 mm Hg till the temperature finally reached 160° C. to remove the water and the unreacted formalin.

The binuclear moiety-content, molecular weight, softening point and viscosity of the resulting novolak phenol resin having a low binuclear moiety-content are listed in the following Table 4.

Example 14

The same procedures for reaction and distillation used in Example 6 were repeated to give a highly pure bisphenol F as a distillate and a novolak phenol resin having a low binuclear moiety-content as a bottom product. The same procedures used in Example 13 were repeated to give a novolak phenol resin having a low binuclear moiety-content except that 5.0% by weight of 37% formalin was used. The binuclear moiety-content, molecular weight, softening point and viscosity of the resulting novolak phenol resin having a low binuclear moiety-content are listed in the following Table 4.

The binuclear moiety-content, the trinuclear moiety-content calculated based on the amount of the resin from which the binuclear moiety-content was subtracted, number-average molecular weight and viscosity of the resulting resin as well as Tg of the hardened product in which the resin was used as a hardener are listed in the following Table 5.

Example 15

The same procedures for reaction and distillation used in Example 6 were repeated to give a highly pure bisphenol F as a distillate and a novolak phenol resin having a low binuclear moiety-content as a bottom product. The same procedures used in Example 13 were repeated to give a novolak phenol resin having a low binuclear moiety-content except that 8.0% by weight of 37% formalin was used.

Figure 7:
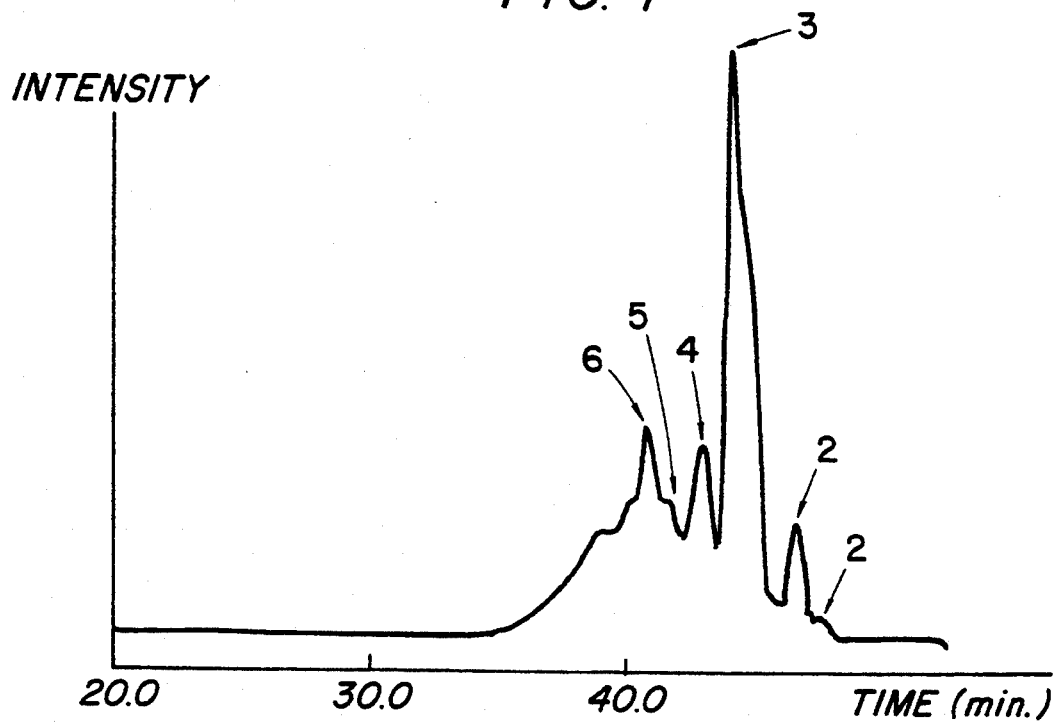
FIG. 7 is a chart showing the distribution of nuclear numbers of moieties present in the phenol resin prepared in Example 15.

The binuclear moiety-content, molecular weight, softening point and viscosity of the resulting novolak phenol resin having a low binuclear moiety-content are listed in Table 4. The binuclear moiety-content, the trinuclear moiety-content calculated based on the amount of the resin from which the binuclear moiety-content was subtracted, number-average molecular weight and viscosity of the resulting resin as well as Tg of the hardened product in which the resin was used as a hardener are listed in Table 5. An analytical chart showing the distribution of nuclear numbers of moieties present in the novolak phenol resin prepared in this Example is shown in FIG. 7.

Example 16

The same procedures for reaction and distillation used in Example 6 were repeated to give a highly pure bisphenol F as a distillate and a novolak phenol resin having a low binuclear moiety-content as a bottom product. The same procedures used in Example 13 were repeated to give a novolak phenol resin having a low binuclear moiety-content except that 10.0% by weight of 37% formalin was used. The binuclear moiety-content, molecular weight, softening point and viscosity of the resulting novolak phenol resin having a low binuclear moiety-content are listed in Table 4.

The binuclear moiety-content, the trinuclear moiety-content calculated based on the amount of the resin from which the binuclear moiety-content was subtracted, number-average molecular weight and viscosity of the resulting resin as well as Tg of the hardened product in which the resin was used as a hardener are listed in Table 5.

Example 17

The same procedures for reaction and distillation used in Example 6 were repeated to give a highly pure bisphenol F as a distillate and a novolak phenol resin having a low binuclear moiety-content as a bottom product. The same procedures used in Example 13 were repeated to give a novolak phenol resin having a low binuclear moiety-content except that 15.0% by weight of 37% formalin was used.

Figure 8:
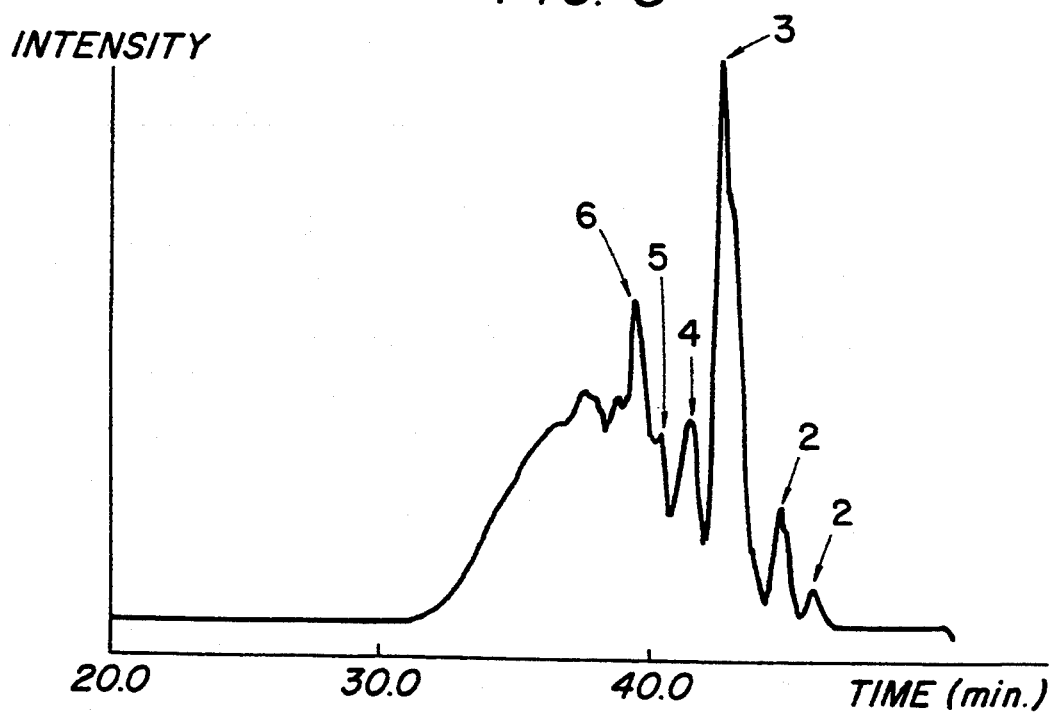
FIG. 8 is a chart showing the distribution of nuclear numbers of moieties present in the phenol resin prepared in Example 17.

The binuclear moiety-content, molecular weight, softening point and viscosity of the resulting novolak phenol resin having a low binuclear moiety-content are listed in Table 4. An analytical chart showing the distribution of nuclear numbers of moieties present in the novolak phenol resin prepared in this Example is shown in FIG. 8.

Example 18

The same procedures for reaction and distillation used in Example 7 were repeated to give a highly pure bisphenol F as a distillate and a novolak phenol resin having a low binuclear moiety-content as a bottom product. The same procedures used in Example 13 were repeated to give a novolak phenol resin having a low binuclear moiety-content except that 10.4% by weight of 37% formalin was used. The binuclear moiety-content, molecular weight, softening point and viscosity of the resulting novolak phenol resin having a low binuclear moiety-content are listed in Table 4.

TABLE 4

| Ex. No. | B.M.-C (wt %) | Mw | Mn | Variance (Mw/Mn) | Softening Point (°C.) | Viscosity (P, at 150° C.) |
|---|---|---|---|---|---|---|
| 13 | 3.8 | 840 | 509 | 1.65 | 86 | 5.4 |
| 14 | 5.8 | 487 | 373 | 1.31 | 75 | 1.0 |
| 15 | 4.6 | 640 | 432 | 1.48 | 86 | 2.5 |
| 16 | 4.1 | 825 | 501 | 1.65 | 94 | 5.3 |
| 17 | 3.3 | 1519 | 708 | 2.15 | 117 | 93.0 |
| 18 | 4.9 | 820 | 500 | 1.64 | 86 | 5.1 |

Note:
Mw: weight-average molecular weight
Mn: number-average molecular weight

Comparative Example 7

The same procedures used in Example 6 were repeated to give a crude bisphenol F except that a mixture of 2000 g of phenol and 1035 g of 37% formalin (P/F=5/3). Then this crude bisphenol F was distilled using an apparatus identical to that used in Example 6 at a pressure of 3 mm Hg till the final temperature reached 220° C. to give a bottom product. The bottom product was cooled to room temperature to give a pasty solid incapable of pulverization.

Figure 9:
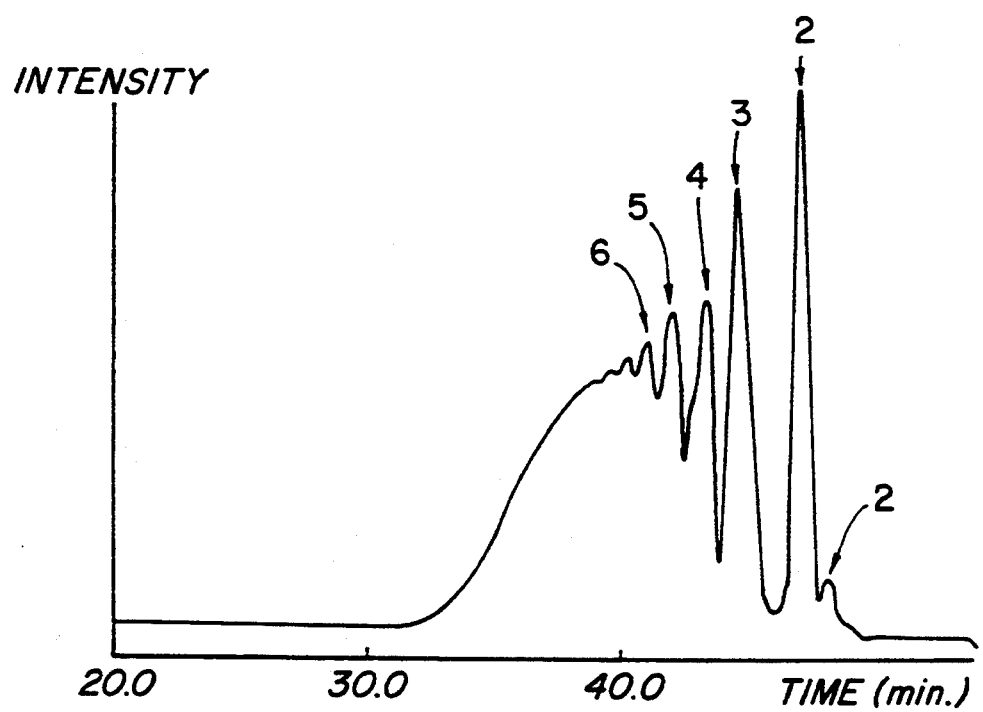
FIG. 9 is a chart showing the distribution of nuclear numbers of moieties present in the phenol resin prepared in Comparative Example 7.

The binuclear moiety-content, the trinuclear moiety-content calculated based on the amount of the bottom product from which the binuclear moiety-content was subtracted, number-average molecular weight and viscosity of the bottom product as well as Tg of the hardened epoxy product are summarized in Table 5. An analytical chart showing the distribution of nuclear numbers of moieties present in the novolak phenol resin prepared in this Comparative Example is shown in FIG. 9.

Comparative Example 8

A reaction was carried out under the same conditions used in Example 6 except that 2000 g of phenol was mixed with 1386 g of a 37% aqueous solution of formalin (P/F=1.24). Then the reaction solution was distilled at a pressure of 3 mm Hg using an apparatus identical to that used in Example 6 till the temperature of the reaction solution was raised up to the final temperature of 175° C. to give a bottom product.

Figure 10:
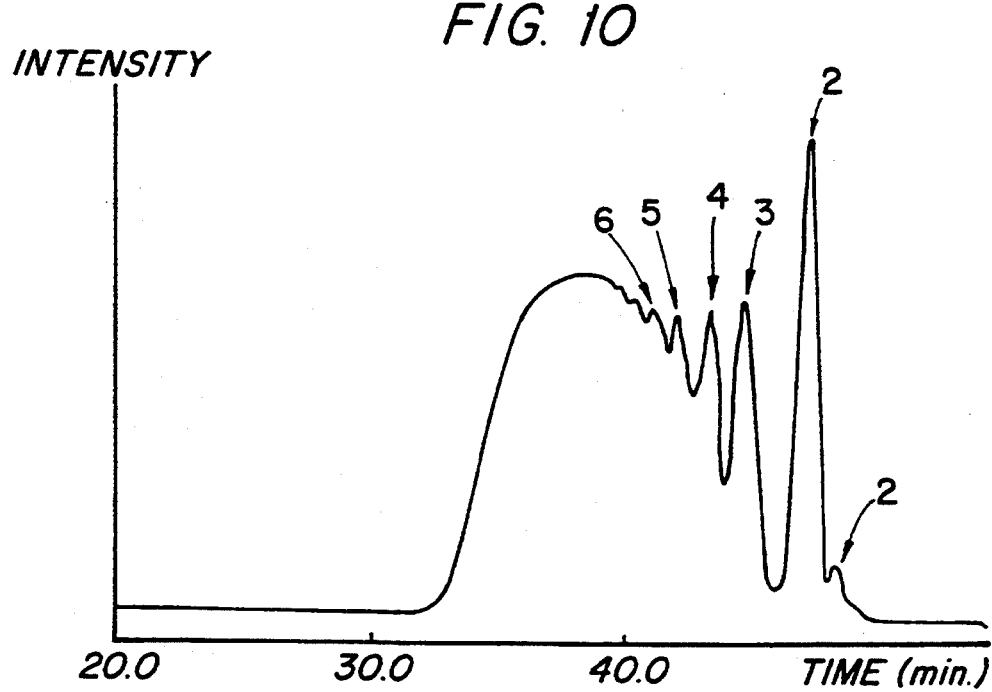
FIG. 10 is a chart showing the distribution of nuclear numbers of moieties present in the phenol resin prepared in Comparative Example 8.

Table 5 shows the binuclear moiety-content of the bottom product, the trinuclear moiety-content calculated based on the amount of the bottom product from which the amount of the binuclear moieties was subtracted, the number-average molecular weight and viscosity of the bottom product and Tg of the hardened product. An analytical chart showing the distribution of nuclear numbers of moieties present in the novolak phenol resin prepared in this Comparative Example is shown in FIG. 10.

TABLE 5

| Ex. No. | 2-Nuclear Moiety-content | 3-Nuclear Moiety-content | Number-average Molecular Weight | Viscosity (P, at 150° C.) | Tg of Hardened Product (°C.) |
|---|---|---|---|---|---|
| 14 | 5.6 | 46.2 | 383 | 1.0 | 178 |
| 15 | 4.6 | 38.9 | 443 | 2.5 | 182 |
| 16 | 4.1 | 34.1 | 513 | 5.3 | 185 |
| 7* | 16.8 | 16.5 | 579 | 4.9 | 166 |
| 8* | 12.0 | 11.0 | 550 | 10.3 | 184 |

*: Comparative Example
Note:
1) Contents are expressed in terms of "% by area".
2) The content of 3-nuclear moieties is calculated based on the amount of the resin from which the binuclear moiety-content is subtracted The method according to the present invention makes the most use of a distillate and the bottom product obtained during distilling a crude bisphenol F obtained through a reaction of phenol and formaldehyde and permits simultaneous preparation of a highly pure bisphenol F and/or a bisphenol F for general use and a novolak phenol resin having a low binuclear moiety-content and/or a high molecular weight novolak phenol resin having a low binuclear moiety-content. Moreover, the method of the present invention generates almost no industrial waste. The method of the present invention also makes it possible to simultaneously prepare a highly pure bisphenol F, a bisphenol F for general use, a novolak phenol resin having a low binuclear moiety-content and a high molecular weight novolak phenol resin having a low binuclear moiety-content in a relative ratio capable of coping with demands through the appropriate control of the molar ratio of phenol to formaldehyde (P/F).

We claim:

1. A method for simultaneously preparing highly pure bisphenol F and a high molecular weight novolak phenol resin comprising the steps of:
   (1) a preparation step comprising reacting phenol with formaldehyde in the presence of an acid catalyst and removing the acid catalyst, water and the unreacted phenol from the resulting reaction product to give a crude bisphenol F;
   (2) a distillation step comprising continuously distilling a part of the crude bisphenol F in a still maintained at a pressure ranging from 1 to 5 mm Hg, while continuously withdrawing a still bottom product to give a highly pure bisphenol F, as a distillate, having a binuclear moiety-content of not less than 95% by weight and a novolak phenol resin, as a still-bottom product, having a binuclear moiety-content of not more than 15% by area; and
   (3) a step for polymerizing the novolak phenol resin with formaldehyde in the presence of an acid catalyst to give a high molecular weight novolak phenol resin.

2. The method for simultaneous preparation as set forth in claim 1 wherein phenol and formaldehyde are reacted at a molar ratio (P/F) ranging from 6 to 30.

3. The method for simultaneous preparation as set forth in claim 1 wherein, in the distillation step, the crude bisphenol F is continuously distilled in a still maintained at a pressure ranging from 1 to 5 mm Hg and a temperature ranging from 220° to 250° C., while continuously supplying the crude bisphenol F to the still, condensing a part of gases generated in the still in a partial condenser, returning the condensate to the still and continuously withdrawing the still-bottom product.

4. The method for simultaneous preparation as set forth in claim 1 wherein, in the distillation step, a distillation apparatus comprising a plurality of stills maintained at a pressure ranging from 1 to 5 mm Hg and a temperature ranging from 200° to 250° C. is provided and the crude bisphenol F is continuously distilled, while the crude bisphenol F is continuously supplied to a first still of the apparatus, the still-bottom product from each still is continuously supplied to each subsequent still; at least a part of evaporated gases discharged from a final still maintained at a temperature ranging from 220° to 250° C. and a pressure ranging from 1 to 5 mm Hg is condensed to return the condensate to the final still and the still-bottom product from the final still is continuously withdrawn.

5. The method for simultaneous preparation as set forth in claim 3 wherein the partial condenser is a multitubular cylindrical heat exchanger or a coil heat exchanger.

6. The method for simultaneous preparation as set forth in claim 3 wherein the partial condensation ratio (weight ratio) ranges from 0.05 to 0.5.

7. The method for simultaneous preparation as set forth in claim 3 wherein the binuclear moiety-content of the distillate is not less than 98% by weight.

8. The method for simultaneous preparation as set forth in claim 3 wherein the binuclear moiety-content of the still-bottom product is not more than 10% by area.

9. The method for simultaneous preparation as set forth in claim 4 wherein the partial condenser is a multitubular cylindrical heat exchanger or a coil heat exchanger.

10. The method for simultaneous preparation as set forth in claim 4 wherein the partial condensation ratio (weight ratio) ranges from 0.05 to 0.5.

11. The method for simultaneous preparation as set forth in claim 4 wherein the binuclear moiety-content of the distillate is not less than 98% by weight.

12. The method for simultaneous preparation as set forth in claim 4 wherein the binuclear moiety-content of the still-bottom product is not more than 10% by area.

13. A method for simultaneously preparing a bisphenol F for general use and a high molecular weight novolak phenol resin comprising the steps of:
   (1) a preparation step comprising reacting phenol with formaldehyde in the presence of an acid catalyst and removing the acid catalyst, water and the unreacted phenol from the resulting reaction product to give a crude bisphenol F;
   (2) a distillation step comprising continuously distilling a part of the crude bisphenol F in a still maintained at a pressure ranging from 1 to 5 mm Hg, while continuously withdrawing a still bottom product to give a highly pure bisphenol F, as a distillate, having a binuclear moiety-content of not less than 95% by weight and a novolak phenol resin, as a still-bottom product, having a binuclear moiety-content of not more than 15% by area;

(3) a step for mixing the highly pure bisphenol F with the remaining crude bisphenol F to give a bisphenol F for general use; and (4) a step for polymerizing the novolak phenol resin with formaldehyde in the presence of an acid catalyst to give a high molecular weight novolak phenol resin.

14. The method for simultaneous preparation as set forth in claim 13 wherein phenol and formaldehyde are reacted at a molar ratio (P/F) ranging from 6 to 30.

15. The method for simultaneous preparation as set forth in claim 13 wherein, in the distillation step, the crude bisphenol F is continuously distilled in a still maintained at a pressure ranging from 1 to 5 mm Hg and a temperature ranging from 220° to 250° C., while continuously supplying the crude bisphenol F to the still, condensing a part of gases generated in the still in a partial condenser, returning the condensate to the still and continuously withdrawing the still-bottom product.

16. The method for simultaneous preparation as set forth in claim 13 wherein, in the distillation step, a distillation apparatus comprising a plurality of stills maintained at a pressure ranging from 1 to 5 mm Hg and a temperature ranging from 200° to 250° C. is provided and the crude bisphenol F is continuously distilled, while the crude bisphenol F is continuously supplied to a first still of the apparatus, the still-bottom product from each still is continuously supplied to each subsequent still; at least a part of evaporated gases discharged from a final still maintained at a temperature ranging from 220° to 250° C. and a pressure ranging from 1 to 5 mm Hg is condensed to return the condensate to the final still and the still-bottom product from the final still is continuously withdrawn.

17. The method for simultaneous preparation as set forth in claim 15 wherein the partial condenser is a multi-tubular cylindrical heat exchanger or a coil heat exchanger.

18. The method for simultaneous preparation as set forth in claim 15 wherein the partial condensation ratio (weight ratio) ranges from 0.05 to 0.5.

19. The method for simultaneous preparation as set forth in claim 15 wherein the binuclear moiety-content of the distillate is not less than 98% by weight.

20. The method for simultaneous preparation as set forth in claim 15 wherein the binuclear moiety-content of the still-bottom product is not more than 10% by area.

21. The method for simultaneous preparation as set forth in claim 16 wherein the partial condenser is a multi-tubular cylindrical heat exchanger or a coil heat exchanger.

22. The method for simultaneous preparation as set forth in claim 16 wherein the partial condensation ratio (weight ratio) ranges from 0.05 to 0.5.

23. The method for simultaneous preparation as set forth in claim 16 wherein the binuclear moiety-content of the distillate is not less than 98% by weight.

24. The method for simultaneous preparation as set forth in claim 16 wherein the binuclear moiety-content of the still-bottom product is not more than 10% by area.

* * * * *

UNITED STATES PATENT AND TRADEMARK OFFICE
CERTIFICATE OF CORRECTION

PATENT NO. : 5,395,915

DATED : March 7, 1995

INVENTOR(S) : limuro et al

It is certified that error appears in the above-indentified patent and that said Letters Patent is hereby corrected as shown below:

On the Title page of Patent, please insert the following information after line [63]:

-- [63] Foreign Application Priority Data

| | | | |
|---|---|---|---|
| February 27, 1992 | [JP] | Japan | 4-041013 |
| February 28, 1992 | [JP] | Japan | 4-042727 |
| July 2, 1992 | [JP] | Japan | 4-175434 |
| July 17, 1992 | [JP] | Japan | 4-190480 |
| September 4, 1992 | [JP] | Japan | 4-237286 -- |

Signed and Sealed this

Thirteenth Day of February, 1996

Attest:

BRUCE LEHMAN

*Attesting Officer*    *Commissioner of Patents and Trademarks*